(12) United States Patent
Linschoten et al.

(10) Patent No.: US 7,354,895 B1
(45) Date of Patent: Apr. 8, 2008

(54) PHOSPHINYLOXY, OXIME AND CARBOXYLIC ACID DERIVATIVES WHICH ARE USEFUL AS CARBOXYPEPTIDASE U INHIBITORS

(75) Inventors: Marcel Linschoten, Västra Frölunda (SE); Magnus Polla, Gothenburg (SE)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 09/600,660

(22) PCT Filed: May 3, 2000

(86) PCT No.: PCT/SE00/00846

§ 371 (c)(1),
(2), (4) Date: Jul. 20, 2000

(87) PCT Pub. No.: WO00/66550

PCT Pub. Date: Nov. 9, 2000

(30) Foreign Application Priority Data

May 3, 1999 (SE) .................................. 9901572

(51) Int. Cl.
C07D 211/08 (2006.01)
C07D 211/20 (2006.01)
C07D 213/72 (2006.01)
A61K 31/44 (2006.01)
A61K 7/02 (2006.01)

(52) U.S. Cl. .............................. 514/2; 514/18; 514/19; 514/63; 514/89; 514/277; 514/340; 514/345; 514/352; 514/354; 514/357; 546/192; 546/210; 546/248; 548/253; 558/166; 558/172; 560/15

(58) Field of Classification Search ............... 558/166, 558/172; 560/15; 546/192, 210, 248; 548/253; 514/2, 18, 19, 63, 89, 277, 340, 345, 352, 514/354, 359
See application file for complete search history.

(56) References Cited

U.S. PATENT DOCUMENTS 2,516,307 A * 7/1950 Floyd ......................... 524/208
4,848,414 A * 7/1989 Cahuzac ..................... 139/411
4,849,414 A * 7/1989 Loots et al. ................... 514/63
5,550,119 A * 8/1996 De Lombaert et al. ....... 514/92
5,672,592 A * 9/1997 Jackson et al. ............... 514/75
5,801,271 A * 9/1998 Seido et al. .................. 560/29

FOREIGN PATENT DOCUMENTS

WO 9837877 9/1998
WO 9838163 9/1998

OTHER PUBLICATIONS

Usik et al , Chemical Abstract vol. 100 No. 85342, "Hydrolysis of the ethyl ester of 4-phenyl-2-pyrrolidone-3-carboxylic acid", 1984.*
Landvatter et al Chem. Abs. vol. 124 No. 145795.*
Gibson et al EP Jol. Med. Chem. V.32 No. 10 pp. 823-831 (1997).*
Fini et al Makro. Chemie V.199 No. 8 pp. 1959-1971 (1987).*
Lindell et al BioOrg. Med. Chem. V.6 No. 5 pp. 547-552 (1996).*
U.S. Appl. No. 09/600,659, filed Jul. 20, 2000, Abrahamsson et al.
U.S. Appl. No. 09/600,661, filed Jul. 20, 2000, Linschoten et al.

* cited by examiner

Primary Examiner—Janet L. Andres
Assistant Examiner—Raymond Covington
(74) Attorney, Agent, or Firm—White & Case LLP

(57) ABSTRACT

The present invention relates to compounds of Formula I, and pharmaceutically acceptable salts or solvates thereof, or solvates of such salts,

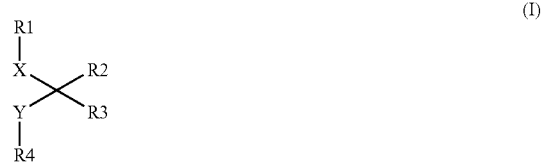

(I)

which compounds inhibit carboxypeptidase U and thus can be used in the prevention and treatment of diseases associated with carboxypeptidase U. In further aspects, the invention relates to compounds of the invention for use in therapy; to processes for preparation of such new compounds; to pharmaceutical compositions containing at least one compound of the invention, or a pharmaceutically acceptable salt or solvate thereof, as active ingredient; and to the use of the active compounds in the manufacture of medicaments for the medical use indicated above.

14 Claims, No Drawings

PHOSPHINYLOXY, OXIME AND CARBOXYLIC ACID DERIVATIVES WHICH ARE USEFUL AS CARBOXYPEPTIDASE U INHIBITORS

FIELD OF THE INVENTION

The present invention relates to novel compounds, and pharmaceutically acceptable salts thereof, which inhibit basic carboxypeptidases, more specifically carboxypeptidase U, and thus can be used in the prevention and treatment of diseases wherein inhibition of carboxypeptidase U is beneficial. In further aspects, the invention relates to compounds of the invention for use in therapy; to processes for preparation of such new compounds; to pharmaceutical compositions containing at least one compound of the invention, or a pharmaceutically acceptable salt thereof, as active ingredient; and to the use of the active compounds in the manufacture of medicaments for the medical use indicated above.

BACKGROUND OF THE INVENTION

Fibrinolysis is the result of a series of enzymatic reactions resulting in the degradation of fibrin by plasmin. The activation of plasminogen is the central process in fibrinolysis. The cleavage of plasminogen to produce plasmin is accomplished by the plasminogen activators, tissue-type plasminogen activator (t-PA) or urokinase-type plasminogen activator (u-PA). Initial plasmin degradation of fibrin generates carboxy-terminal lysine residues that serves as high-affinity binding sites for plasminogen. Since plasminogen bound to fibrin is much more readily activated to plasmin than free plasminogen, this mechanism provides a positive feedback regulation of fibrinolysis.

One of the endogenous inhibitors to fibrinolysis is carboxypeptidase U (CPU). CPU is also known as plasma carboxypeptidase B, active thrombin activatable fibrinolysis inhibitor (TAFIa), carboxypeptidase R and inducible carboxypeptidase activity. CPU is formed during coagulation and fibrinolysis from its precursor proCPU by the action of proteolytic enzymes, e.g. thrombin, thrombin-thrombomodulin complex or plasmin. CPU cleaves basic amino acids at the carboxy-terminal of fibrin fragments. The loss of carboxy-terminal lysines and thereby of lysine binding sites for plasminogen then serves to inhibit fibrinolysis.

By inhibiting the loss of lysine binding sites for plasminogen and thus increasing the rate of plasmin formation, effective inhibitors of carboxypeptidase U would be expected to facilitate fibrinolysis.

2-mercaptomethyl-3-guanidinoethylthiopropanoic acid is reported as a carboxypeptidase N inhibitor. More recently, this compound has been shown to inhibit CPU, Hendriks, D. et al., Biochemica et Biophysica Acta, 1034 (1990) 86-92.

Guanidinoethylmercaptosuccinic acid is reported as a carboxypeptidase N inhibitor. More recently, this compound has been shown to inhibit CPU, Eaton, D. L., et al., The Journal of Biological Chemistry, 266 (1991) 21833-21838.

DISCLOSURE OF THE INVENTION

It has surprisingly been found that compounds of the Formula I are particularly effective as inhibitors of carboxypeptidase U and thereby useful as medicaments for the treatment or prophylaxis of conditions wherein inhibition of carboxypeptidase U is beneficial.

In one aspect, the invention thus relates to compounds of the general Formula I,

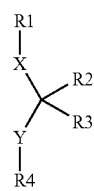

(I)

or a pharmaceutically acceptable salt or solvate thereof, or a solvate of such a salt, wherein $R_1$ represents, $C_1$-$C_6$ alkyl, substituted with one or more basic groups such as amino, amidino and/or guanidino;

cycloalkyl, substituted with one or more basic groups such as amino, amidino and/or guanidino;

heterocyclyl, containing at least one nitrogen atom;

heterocyclyl, containing at least one hetero atom selected from S or O, and substituted with one or more basic groups such as amino, amidino and/or guanidino;

or aryl, substituted with one or more basic groups such as amino, amidino and/or guanidino, $R_2$ represents H, acyl, acylamino, alkyl, alkylcarbamoyl, alkylthio, alkoxy, aroyl, aroylamino, aryloxy, arylthio, amidino, amino, aryl, carbamoyl, carboxy, cyano, cycloalkyl, formyl, guanidino, halogen, heterocyclyl, hydroxy, oxo, nitro, thiol, $Z_2N\text{—}CO\text{—}O\text{—}$, $ZO\text{—}CO\text{—}NZ\text{—}$ or $Z_2N\text{—}CO\text{—}NZ\text{—}$ group, $R_3$ represents $COOR_5$, $SO(OR_5)$, $SO_3R_5$, $P\!\!=\!\!O(OR_5)_2$, $B(OR_5)_2$, $P\!\!=\!\!OR_5(OR_5)$, or tetrazole, or any carboxylic acid isostere, $R_4$ represents a

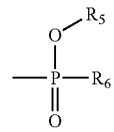

-group, or a

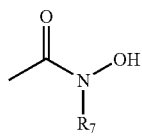

-group, or a

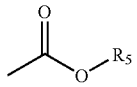

-group, $R_5$ represents H, $C_1$-$C_6$ alkyl or aryl, $R_6$ represents $C_1$-$C_6$ alkyl, aryl, cycloalkyl, heterocyclyl, or an optionally N-substituted $H_2N$—C(Z)—CONH—C(Z)— or $H_2N$—C(Z)— group, $R_7$ represents H or $C_1$-$C_6$ alkyl, X represents O, S, SO, $SO_2$, $C(Z)_2$, N(Z), $NR_7SO_2$, $SO_2NR_7$, $NR_7CO$ or $CONR_7$, Y represents O, N(Z), S, $C(Z)_2$, or a single bond, Z represents independently H, $C_1$-$C_6$ alkyl, aryl, cycloalkyl or heterocyclyl, with the proviso that when X represents O, S, SO, $SO_2$, N(Z), $NR_7SO_2$, $SO_2NR_7$, or $NR_7CO$ then Y represents $C(Z)_2$ or a single bond.

Preferred compounds according to the present invention are those of Formula I, or a pharmaceutically acceptable salt or solvate thereof, or a solvate of such a salt, wherein $R_1$ represents,
- $C_1$-$C_6$ alkyl, substituted with one or more basic groups such as amino, amidino and/or guanidino;
- cycloalkyl, substituted with one or more basic groups such as amino, amidino and/or guanidino;
- heterocyclyl, containing at least one nitrogen atom;
- heterocyclyl, containing at least one hetero atom selected from S or O, and substituted with one or more basic groups such as amino, amidino and/or guanidino;
- or aryl, substituted with one or more basic groups such as amino, amidino and/or guanidino, $R_2$ represents H, acyl, acylamino, alkyl, alkylcarbamoyl, alkylthio, alkoxy, aroyl, aroylamino, aryloxy, arylthio, amidino, amino, aryl, carbamoyl, carboxy, cyano, cycloalkyl, formyl, guanidino, halogen, heterocyclyl, hydroxy, oxo, nitro, thiol, $Z_2N$—CO—O—, ZO—CO—NZ— or $Z_2N$—CO—NZ— group, $R_3$ represents $COOR_5$, $R_4$ represents a

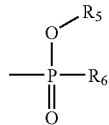

-group, or a

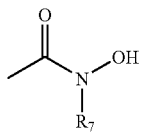

-group, or a

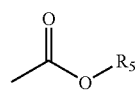

-group, $R_5$ represents H, $C_1$-$C_6$ alkyl or aryl, $R_6$ represents $C_1$-$C_6$ alkyl, aryl, cycloalkyl, heterocyclyl, or an optionally N-substituted $H_2N$—C(Z)—CONH—C(Z)— or $H_2N$—C(Z)— group, $R_7$ represents H or $C_1$-$C_6$ alkyl, X represents $C(Z)_2$, Y represents O, N(Z), S, $C(Z)_2$, or a single bond, Z represents independently H, $C_1$-$C_6$ alkyl, aryl, cycloalkyl or heterocyclyl.

More preferred compounds according to the present invention are those of Formula I, or a pharmaceutically acceptable salt or solvate thereof, or a solvate of such a salt, wherein $R_1$ represents,
- cycloalkyl, substituted with one or more basic groups such as amino, amidino and/or guanidino;
- heterocyclyl, containing at least one nitrogen atom;
- heterocyclyl, containing at least one hetero atom selected from S or O, and substituted with one or more basic groups such as amino, amidino and/or guanidino;

$R_2$ represents H, $C_1$-$C_3$ alkyl, amino, halogen or hydroxy, $R_3$ represents $COOR_5$, $R_4$ represents a

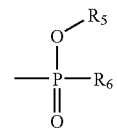

-group, $R_5$ represents H, $C_1$-$C_6$ alkyl or aryl, $R_6$ represents $C_1$-$C_6$ alkyl, aryl, cycloalkyl, heterocyclyl, or an optionally N-substituted $H_2N$—C(Z)—CONH—C(Z)— or $H_2N$—C(Z)— group, X represents $C(Z)_2$, Y represents O or $C(Z)_2$, Z represents independently H or $C_1$-$C_6$ alkyl.

Other more preferred compounds according to the present invention are those of Formula I, or a pharmaceutically acceptable salt or solvate thereof, or a solvate of such a salt, wherein $R_1$ represents,
- cycloalkyl, substituted with one or more basic groups such as amino, amidino and/or guanidino;
- heterocyclyl, containing at least one nitrogen atom;
- heterocyclyl, containing at least one hetero atom selected from S or O, and substituted with one or more basic groups such as amino, amidino and/or guanidino;

$R_2$ represents H, $C_1$-$C_3$ alkyl, amino, halogen or hydroxy, $R_3$ represents $COOR_5$, $R_4$ represents a

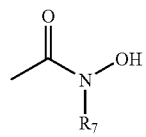

-group, $R_5$ represents H, $C_1$-$C_6$ alkyl or aryl, $R_7$ represents H or $C_1$-$C_6$ alkyl, X represents $C(Z)_2$, Y represents $C(Z)_2$ or a single bond, Z represents independently H or $C_1$-$C_6$ alkyl.

Yet other more preferred compounds according to the present invention are those of Formula I, or a pharmaceutically acceptable salt or solvate thereof, or a solvate of such a salt, wherein $R_1$ represents,
cycloalkyl, substituted with one or more basic groups such as amino, amidino and/or guanidino;
heterocyclyl, containing at least one nitrogen atom;
heterocyclyl, containing at least one hetero atom selected from S or O, and substituted with one or more basic groups such as amino, amidino and/or guanidino;

$R_2$ represents H, $C_1$-$C_3$ alkyl, amino, halogen or hydroxy,
$R_3$ represents COOR$_5$,
$R_4$ represents a

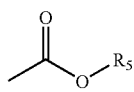

-group,
$R_5$ represents H, $C_1$-$C_6$ alkyl or aryl,
X represents $C(Z)_2$,
Y represents $C(Z)_2$ or a single bond,
Z represents independently H or $C_1$-$C_6$ alkyl, Even more preferred compounds according to the present invention are those of Formula I, or a pharmaceutically acceptable salt or solvate thereof, or a solvate of such a salt, wherein $R_1$ represents,
cycloalkyl, substituted with one or more basic groups such as amino, amidino and/or guanidino;
heterocyclyl, containing at least one nitrogen atom;

$R_2$ represents H, F, $C_1$ alkyl,
$R_3$ represents COOR$_5$,
$R_4$ represents a

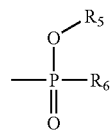

-group,
$R_5$ represents H, $C_1$-$C_6$ alkyl or aryl,
$R_6$ represents $C_1$-$C_6$ alkyl, aryl, cycloalkyl, heterocyclyl, or an optionally N-substituted H$_2$N—C(Z)—CONH—C(Z)— or H$_2$N—C(Z)— group,
X represents $C(Z)_2$,
Y represents O or $C(Z)_2$,
Z represents independently H or $C_1$-$C_6$ alkyl.

Other even more preferred compounds according to the present invention are those of Formula I, or a pharmaceutically acceptable salt or solvate thereof, or a solvate of such a salt, wherein $R_1$ represents,
cycloalkyl, substituted with one or more basic groups such as amino, amidino and/or guanidino;
heterocyclyl, containing at least one nitrogen atom;

$R_2$ represents H, F, $C_1$ alkyl,
$R_3$ represents COOR$_5$,
$R_4$ represents a

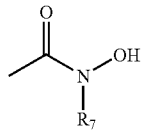

-group,
$R_5$ represents H, $C_1$-$C_6$ alkyl or aryl,
$R_7$ represents H or $C_1$-$C_6$ alkyl,
X represents $C(Z)_2$,
Y represents $C(Z)_2$ or a single bond,
Z represents independently H or $C_1$-$C_6$ alkyl.

Yet other even more preferred compounds according to the present invention are those of Formula I, or a pharmaceutically acceptable salt or solvate thereof, or a solvate of such a salt, wherein $R_1$ represents,
cycloalkyl, substituted with one or more basic groups such as amino, amidino and/or guanidino;
heterocyclyl, containing at least one nitrogen atom;

$R_2$ represents H, F, $C_1$ alkyl,
$R_3$ represents COOR$_5$,
$R_4$ represents a

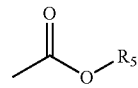

-group,
$R_5$ represents H, $C_1$-$C_6$ alkyl or aryl,
X represents $C(Z)_2$,
Y represents $C(Z)_2$ or a single bond,
Z represents independently H or $C_1$-$C_6$ alkyl.

Most preferred compounds according to the present invention are those of Formula I, or a pharmaceutically acceptable salt or solvate thereof, or a solvate of such a salt, wherein $R_1$ represents pyridyl or piperidinyl,
$R_2$ represents H,
$R_3$ represents COOR$_5$,
$R_4$ represents a

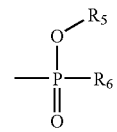

-group,
$R_5$ represents H,
$R_6$ represents $C_1$-$C_6$ alkyl or an optionally N-substituted H$_2$N—C(Z)—CONH—C(Z)— or H$_2$N—C(Z)— group,
X represents CHZ,
Y represents CHZ,
Z represents independently H or $C_1$-$C_6$ alkyl.

Other most preferred compounds according to the present invention are those of Formula I, or a pharmaceutically acceptable salt or solvate thereof, or a solvate of such a salt, wherein R₁ represents pyridyl or piperidinyl,
R₂ represents H,
R₃ represents COOR₅,
R₄ represents a

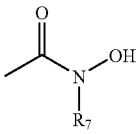

-group,
R₅ represents H,
R₇ represents H,
X represents CHZ,
Y represents CHZ or a single bond,
Z represents independently H or $C_1$-$C_6$ alkyl.

Yet other most preferred compounds according to the present invention are those of Formula I, or a pharmaceutically acceptable salt or solvate thereof, or a solvate of such a salt, wherein
R₁ represents pyridyl or piperidinyl,
R₂ represents H,
R₃ represents COOR₅,
R₄ represents a

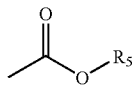

-group,
R₅ represents H,
X represents CHZ,
Y represents CHZ or a single bond,
Z represents independently H or $C_1$-$C_6$ alkyl.

The following definitions shall apply throughout the specification and the appended claims:

The term "basic group" denotes a basic group, wherein the conjugate acid of said basic group has a pKa of from about −5 to about 25, preferably of from 1 to 15.

The term "carboxylic acid isostere" denotes an acidic group having a pKa of from about −5 to about 25, preferably of from 1 to 15.

The term "$C_1$-$C_6$ alkyl" denotes a straight or branched, saturated or unsaturated, substituted or unsubstituted alkyl group having 1 to 6 carbon atoms in the chain wherein the alkyl group may optionally be interrupted by one or more heteroatoms selected from O, N or S. Examples of said alkyl include, but is not limited to, methyl, ethyl, ethenyl, ethynyl, n-propyl, iso-propyl, propenyl, iso-propenyl, propynyl, n-butyl, iso-butyl, sec-butyl, t-butyl, butenyl, iso-butenyl, butynyl and straight- and branched-chain pentyl and hexyl.

The term "$C_1$-$C_3$ alkyl" denotes a straight or branched, saturated or unsaturated, substituted or unsubstituted alkyl group having 1 to 3 carbon atoms in the chain wherein the alkyl group may optionally be interrupted by one or more heteroatoms selected from O, N or S. Examples of said alkyl include, but is not limited to, methyl, ethyl, ethenyl, ethynyl, n-propyl, iso-propyl, propenyl, iso-propenyl, propynyl.

The term "$C_1$ alkyl" denotes a substituted or unsubstituted alkyl group having 1 carbon atom. An example of said alkyl include, but is not limited to, methyl.

The term "$C_1$-$C_6$ alkoxy" denotes an alkyl-O-group, wherein $C_1$-$C_6$ alkyl is as defined above.

The term "$C_1$-$C_3$ alkoxy" denotes an alkyl-O-group, wherein $C_1$-$C_3$ alkyl is as defined above.

The term "heterocyclyl" denotes a substituted or unsubstituted, 4- to 10-membered monocyclic or multicyclic ring system in which one or more of the atoms in the ring or rings is an element other than carbon, for example nitrogen, oxygen or sulfur, especially 4-, 5- or 6-membered aromatic or alifatic hetorocyclic groups, and includes, but is not limited to azetidine, furan, thiophene, pyrrole, pyrroline, pyrrolidine, dioxolane, oxathiolane, oxazolane, oxazole, thiazole, imidazole, imidazoline, imidazolidine, pyrazole, pyrazoline, pyrazolidine, isoxazole, isothiazole, oxadiazole, furazan, triazole, thiadiazole, pyran, pyridine, piperidine, dioxane, morpholine, dithiane, oxathiane, thiomorpholine, pyridazine, pyrimidine, pyrazine, piperazine, triazine, thiadiazine, dithiazine, azaindole, azaindoline, indole, indoline, naphthyridine groups, and shall be understood to include all isomers of the above identified groups. The term "azetidinyl" shall for example by understood to include the 2-, and 3-isomers and the terms "pyridyl" and "piperidinyl" shall for example by understood to include the 2-, 3-, and 4-isomers.

The term "cycloalkyl" denotes a saturated or unsaturated, substituted or unsubstituted, non-aromatic ring composed of 3, 4, 5, 6 or 7 carbon atoms, and includes, but is not limited to, cyclopropyl, cyclobutyl, cyclopentyl, cyclohexyl, cycloheptyl, cyclobutenyl, cyclopentenyl, cyclohexenyl, cycloheptenyl, cyclopentadienyl, cyclohexadienyl and cycloheptadienyl groups.

The term "halogen" includes fluoro, chloro, bromo and iodo groups.

The term "aryl" denotes a substituted or unsubstituted $C_6$-$C_{14}$ aromatic hydrocarbon and includes, but is not limited to, phenyl, naphthyl, indenyl, anthracenyl, phenanthrenyl, and fluorenyl.

The term "aryloxy" denotes an aryl-O-group, wherein aryl is as defined above.

The term "acyl" denotes an alkyl-CO-group, wherein alkyl is as defined above.

The term "aroyl" denotes an aryl-CO-group, wherein aryl is as defined above.

The term "alkylthio" denotes an alkyl-S-group, wherein alkyl is as defined above.

The term "arylthio" denotes an aryl-S-group, wherein aryl is as defined above.

The term "aroylamino" denotes an aroyl-N(Z)-group, wherein aroyl and Z is as defined above.

The term "acylamino" denotes an acyl-N(Z)-group, wherein acyl and Z is as defined above.

The term "carbamoyl" denotes a $H_2N$—CO-group.

The term "alkylcarbamoyl" denotes a $Z_2N$—CO-group wherein Z is as defined above.

The term "substituted" denotes an "$C_1$ alkyl", "$C_1$-$C_3$ alkyl", "$C_1$-$C_6$ alkyl", "cycloalkyl", "heterocyclyl", "aryl", $H_2N$—C(Z)—CONH—C(Z)— or a $H_2N$—C(Z)— group as defined above which is substituted by one or more acyl, acylamino, alkyl, alkylcarbamoyl, alkylthio, alkoxy, aroyl, aroylamino, aryloxy, arylthio, amidino, amino, aryl, carbamoyl, carboxy, cyano, cycloalkyl, formyl, guanidino, halogen, heterocyclyl, hydroxy, oxo, nitro, thiol, thio, $Z_2N$—CO—O—, ZO—CO—NZ—, or $Z_2N$—CO—NZ— groups.

Both the pure enantiomers, racemic mixtures and unequal mixtures of two enantiomers are within the scope of the present invention. It should also be understood that all the diastereomeric forms possible are within the scope of the invention. Also included in the invention are derivatives of the compounds of the Formula I which have the biological function of the compounds of Formula I, such as prodrugs.

Depending on the process conditions the compounds of Formula I are obtained either in neutral or salt form or as a solvate, e.g. a hydrate, and are all within the scope of the present invention.

PREPARATION

The present invention also provides the process A-C for the manufacture of compounds with the general Formula I.

Process A

Process A for manufacture of compounds with the general Formula I, wherein $R_1$, $R_5$, $R_6$, and Z are as defined above and $R_2$ is H, $R_3$ is $COOR_5$, $R_4$ represents a

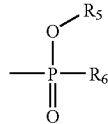

-group, X is $C(Z)_2$, Y is $C(Z)_2$ and comprises the following steps:

a) Compounds of the general Formula II,

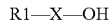 (II)

wherein $R_1$ and Z is as defined for Formula I and X is $C(Z)_2$, which are either commercially available or are available using known techniques, can be converted into a compound of the general Formula III,

 (III)

wherein L is a suitable leaving group, such as a chloro, bromo, iodo, triflate or tosyl group, under standard conditions using a suitable reagent, such as $PPh_3/CBr_4$, TosCl/ pyridine or $(CF_3SO_2)_2O/TEA$).

b) Compounds of the general Formula III can thereafter be reacted with compounds of the general Formula IV,

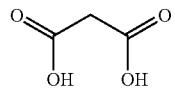 (IV)

which are either commercially available or are available using known technics, in the presence of a suitable base, such as $K_2CO_3$ or NaH, under standard conditions to give compounds of the general Formula V,

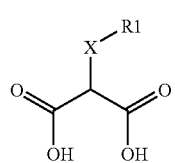 (V)

c) Compounds of the general Formula V can thereafter be converted to compounds of the general Formula VI,

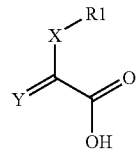 (VI)

by treatment with formaldehyde in the presence of a suitable base, such as $Et_2NH$, under standard conditions.

However, if Y is CH(Z) then compounds of the general Formula VI can be prepared by treating compounds of the general Formula VII,

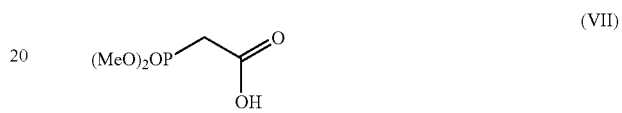 (VII)

with an alkylating agent of the general Formula III,

 (III)

wherein $R_1$ is as defined for Formula I and L is a suitable leaving group, such as a chloro, bromo, iodo, triflate or tosyl group, in the presence of a suitable base, such as LDA or NaH, under standard conditions to give compounds of the general Formula VIII,

 (VIII)

Compounds of the general Formula VIII can thereafter be reacted with an appropriate aldehyde CHO(Z), wherein Z is as defined for Formula I, in the presence of a suitable base, such as KOtBu, LDA or NaH, under standard conditions to give a compound of the general Formula VI.

d) Compounds of the general Formula VI can be further reacted with compounds of the general Formula IX

 (IX)

wherein $R_6$ is as defined for Formula I, in the presence of a suitable reagent, such as BSA or HMDS, under standard conditions to give compounds of the general Formula I, wherein $R_1$, $R_5$, $R_6$ and Z are as defined above, $R_2$ is H, $R_3$ is $COOR_5$, $R_4$ represents a

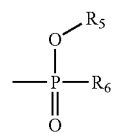

-group, X is $C(Z)_2$, and Y is $C(Z)_2$.

Process B

Process B for manufacture of compounds with the general Formula I, wherein $R_1$, $R_2$, $R_5$, $R_6$, and Z are as defined above and $R_3$ is $COOR_5$, X is $C(Z)_2$, Y is O, and $R_4$ represents a

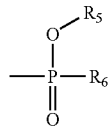

-group, comprises the following steps:

a) Reacting a compound of the general Formula X,

 (X)

wherein $R_1$, $R_2$ and Z are as defined in Formula I and X is $C(Z)_2$ in the presence of suitable reagents, such as TMSCN/$ZnI_2$ or KCN/HOAc, under standard conditions to give compounds of the general Formula XI,

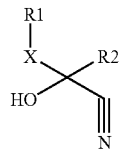 (XI)

wherein $R_1$ and $R_2$ are as defined in Formula I and X is $C(Z)_2$.

b) Compounds of the general Formula XI can thereafter be treated with suitable reagents, such as HCl or HCl/MeOH, under standard conditions to give compounds of the general Formula XII,

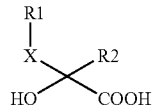 (XII)

wherein $R_1$ and $R_2$ are as defined in Formula I and X is $C(Z)_2$.

c) Compounds of the general Formula XII can thereafter be reacted with compounds of the general Formula XIII,

 (XIII)

wherein $R_6$ is as defined in the general Formula I, which are either commercially available, well known in the literature, or are available using known techniques, in the presence of suitable coupling reagents such a DCC/DMAP, PyBop/DIPEA or $SOCl_2$, under standard conditions to give compounds of the general Formula I, wherein $R_1$, $R_2$, $R_5$, $R_6$ and Z are as defined above, $R_3$ is $COOR_5$, $R_4$ represents a

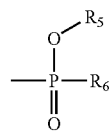

-group, X is $C(Z)_2$ and Y is O.

Process C

Process C for manufacture of compounds with the general Formula I, wherein $R_1$ and $R_2$ are as defined above, X is $C(Z)_2$, Y is $C(Z)_2$ or a single bond, and $R_3$ and $R_4$ are $COOR_5$, comprises the following steps, a) reacting a compound of the general Formula XIV,

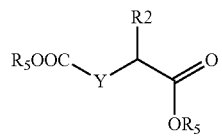 (XIV)

wherein $R_2$ and $R_5$ are as defined in Formula I and Y is $C(Z)_2$ or a single bond, which are either commercially available, well known in the literature, or are available using known techniques, with a compound of the general Formula III,

 (III)

wherein $R_1$ is as defined for Formula I, X is $C(Z)_2$ and L is a suitable leaving group, such as Cl, Br, I or tosyl, in the presence of a suitable base, such as LDA or NaH under standard conditions, to give a compound of the general Formula XV,

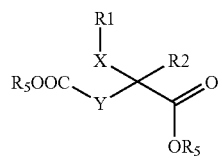 (XV)

b) hydrolysing a compound of the general Formula XV, for example by treatment with aqueous NaOH or aqueous TFA under standard conditions to give compounds of the general Formula I, wherein $R_1$ and $R_2$ are as defined above, X is $C(Z)_2$, Y is $C(Z)_2$ or a single bond, and $R_3$ and $R_4$ are COOH.

Process D

Process D for manufacture of compounds with the general Formula I, wherein $R_1$, $R_2$, $R_5$, $R_7$, X, Y and Z are as defined above, $R_3$ is $COOR_5$ and $R_4$ represents a

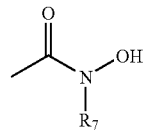

-group, comprises the following steps:

a) Compounds of the general Formula XV,

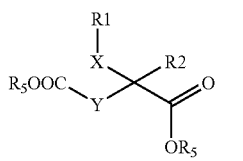
(XV)

can be reacted with compounds of the general Formula XVI,

 (XVI)

wherein $R_7$ is as defined in Formula I, in the presence of suitable reagents, such as DCC/DMAP, under standard conditions, to give compounds of the general Formula I, wherein $R_1$, $R_2$, $R_5$, $R_7$, X, Y and Z are as defined above, $R_3$ is $COOR_5$ and $R_4$ represents a

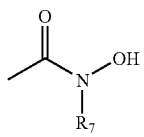

-group.

It will be appreciated by those skilled in the art that in the process described above the functional groups of intermediate compounds may need to be protected by protecting groups.

Functional groups which it is desirable to protect include hydroxy, amino, mercapto and carboxylic acid. Suitable protecting groups for hydroxy include trialkylsilyl or diarylalkylsilyl (e.g. t-butyldimethylsilyl, t-butyldiphenylsilyl or trimethylsilyl), tetrahydropyranyl and benzyl. Suitable protecting groups for amino, amidino and guanidino include t-butyloxycarbonyl and benzyloxycarbonyl. Suitable protecting groups for mercapto include $CO-C_{1-6}$ alkyl, p-methoxybenzyl and trityl. Suitable protecting groups for carboxylic acid include $C_{1-6}$ alkyl and benzyl esters.

Protecting groups may be removed in accordance with techniques which are well known to those skilled in the art and as described hereinafter.

Certain protected derivatives of compounds of Formula I, which may be made prior to a final deprotection stage to form compounds of Formula I, are novel.

The use of protecting groups is described in 'Protective Groups in Organic Synthesis', 2nd edition, T. W. Greene & P. G. M. Wutz, Wiley-Interscience (1991). The protective group may also be a polymer resin such as Wang resin or a 2-chorotrityl chloride resin.

It will also be appreciated by those skilled in the art, although such protected derivatives of compounds of Formula I may not possess pharmacological activity as such, they may be administered parenterally or orally and thereafter metabolised in the body to form compounds of the invention which are pharmacologically active. Such derivatives may therefore be described as "prodrugs". All prodrugs of compounds of Formula I are included within the scope of the invention.

It should also be understood that all polymorphs, amorphous forms, anhydrates, hydrates, solvates of the compounds of the present invention are within the scope of the invention.

Pharmaceutical Formulations

In yet a further aspect, the invention relates to pharmaceutical compositions containing at least one compound of the present invention, or a pharmaceutically acceptable salt thereof, as active ingredient.

For clinical use, the compounds of the invention are formulated into pharmaceutical formulations for oral, intravenous, subcutaneous, tracheal, bronchial, intranasal, pulmonary, transdermal, buccal, rectal, parenteral or other mode of administration. The pharmaceutical formulation contains a compound of the invention in combination with one or more pharmaceutically acceptable ingredients. The carrier may be in the form of a solid, semi-solid or liquid diluent, or a capsule. These pharmaceutical preparations are a further object of the invention. Usually the amount of active compounds is between 0.1-95% by weight of the preparation.

In the preparation of pharmaceutical formulations containing a compound of the present invention the compound selected may be mixed with solid, powdered ingredients, such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture may then be processed into granules or pressed into tablets.

Soft gelatine capsules may be prepared with capsules containing a mixture of the active compound or compounds of the invention, vegetable oil, fat, or other suitable vehicle for soft gelatine capsules. Hard gelatine capsules may contain granules of the active compound. Hard gelatine capsules may also contain the active compound in combination with solid powdered ingredients such as lactose, saccharose, sorbitol, mannitol, potato starch, corn starch, amylopectin, cellulose derivatives or gelatine.

Dosage units for rectal administration may be prepared (i) in the form of suppositories which contain the active substance mixed with a neutral fat base; (ii) in the form of a gelatine rectal capsule which contains the active substance in a mixture with a vegetable oil, paraffin oil or other suitable vehicle for gelatine rectal capsules; (iii) in the form of a ready-made micro enema; or (iv) in the form of a dry micro enema formulation to be reconstituted in a suitable solvent just prior to administration.

Liquid preparations may be prepared in the form of syrups or suspensions, e.g. solutions or suspensions containing the active ingredient and the remainder consisting, for example, of sugar or sugar alcohols and a mixture of ethanol, water, glycerol, propylene glycol and polyethylene glycol. If desired, such liquid preparations may contain colouring agents, flavouring agents, preservatives, saccharine and carboxymethyl cellulose or other thickening agents. Liquid preparations may also be prepared in the form of a dry powder to be reconstituted with a suitable solvent prior to use.

Solutions for parenteral administration may be prepared as a solution of a compound of the invention in a pharmaceutically acceptable solvent. These solutions may also contain stabilizing ingredients and/or buffering ingredients. Solutions for parenteral administration may also be prepared as a dry preparation to by reconstituted with a suitable solvent before use.

The typical daily dose of the active substance varies within a wide range and will depend on various factors such as for example the individual requirement of each patient, the route of administration and the disease. In general, oral and parenteral dosages will be in the range of 0.1 to 1000 mg per day of active substance.

Medical and Pharmaceutical Use

The compounds of the invention are inhibitors of carboxypeptidase U either as such or, in the case of prodrugs, after administration. The compounds of the invention are thus expected to be useful in those conditions where inhibition of carboxypeptidase U is beneficial, such as in the treatment or prophylaxis of thrombosis and hypercoagulability in blood and tissues of mammals, including man.

It is known that hypercoagulability may lead to thrombo-embolic diseases. Conditions associated with hypercoagulability and thrombo-embolic diseases which may be mentioned include protein C resistance and inherited or acquired deficiencies in antithrombin III, protein C, protein S and heparin cofactor II. Other conditions known to be associated with hypercoagulability and thrombo-embolic disease include circulatory and septic shock, circulating antiphospholipid antibodies, homocysteinemia, heparin-induced thrombocytopenia and defects in fibrinolysis. The compounds of the invention are thus indicated both in the therapeutic and/or prophylactic treatment of these conditions. The compounds of the invention are further indicated in the treatment of conditions where there is an undesirable excess of proCPU/CPU.

Particular disease states which may be mentioned include the therapeutic and/or prophylactic treatment of venous thrombosis and pulmonary embolism, arterial thrombosis (e.g. in myocardial infarction, unstable angina, thrombosis-based stroke and peripheral arterial thrombosis) and systemic embolism usually from the atrium during arterial fibrillation or from the left ventricle after transmural myocardial infarction.

Moreover, the compounds of the invention are expected to have utility in prophylaxis of re-occlusion and restenosis (i.e. thrombosis) after thrombolysis, percutaneous transluminal angioplasty (PTA) and coronary bypass operations; the prevention of re-thrombosis after microsurgery and vascular surgery in general.

Further indications include the therapeutic and/or prophylactic treatment of disseminated intravascular coagulation caused by bacteria, multiple trauma, intoxication or any other mechanism, fibrinolytic treatment when blood is in contact with foreign surfaces in the body, such as vascular grafts, vascular stents, vascular catheters, mechanical and biological prosthetic valves or any other medical device, and fibrinolytic treatment when blood is in contact with medical devices outside the body, such as during cardiovascular surgery using a heart-lung machine or in haemodialysis.

The compounds of the invention may also be combined and/or coadministered with any antithrombotic agent with a different mechanism of action, such as the antiplatelet agents acetylsalicylic acid ticlopidine, clopidogrel, thromboxane receptor and/or synthetase inhibitors, fibrinogen receptor antagonists, prostacyclin mimetics and phosphodiesterase inhibitors and ADP-receptor ($P_2T$) antagonists and thrombin inhibitors.

The compounds of the invention may further be combined and/or coadministered with thrombolytics such as tissue plasminogen activator (natural, recombinant or modified), streptokinase, urokinase, prourokinase, anisoylated plasminogen-streptokinase activator complex (APSAC), animal salivary gland plasminogen activators, and the like in the treatment of thrombotic diseases, in particular myocardial infarction and stroke.

In vitro Experiments

The inhibiting effect of the compounds of the present invention was estimated using the assay described in: Dirk Hendriks, Simon Scharpé and Marc van Sande, Clinical Chemistry, 31, 1936-1939 (1985); and Wei Wang, Dirk F. Hendriks, Simon S. Scharpé, The Journal of Biological Chemistry, 269, 15937-15944 (1994).

EXAMPLES

General Experimental Procedures

Mass spectra were recorded on a Finnigan MAT TSQ 700 triple quadropole mass spectrometer equipped with an electrospray interface (FAB-MS) and VG Platform II mass spectrometer equipped with an electrospray interface (LC-MS). $^1$H NMR and $^{13}$C NMR measurements were performed on Varian UNITY plus 400, 500 and 600 spectrometers, operating at $^1$H frequencies of 400, 500 and 600 MHz respectively. Chemical shifts are given in ppm with the solvent as internal standard. Organic extracts were dried using $MgSO_4$ or $Na_2SO_4$ as the drying agent. Chromatography separations were performed using Merck Silica gel 60 (0.063-0.200 mm). HPLC separations were performed on a HIGHCROM KR100-10C8 column.

Example 1

5-Amino-2-[(1-benzyloxycarbonylamino-2-methyl-propyl)-hydroxy-phosphinoyloxy]-pentanoic acid (a) 5-tert-Butoxycarbonylamino-2-hydroxy-pentanoic acid Di-t-butyl dicarbonate (30.8 g, 0.141 mol) was added in portions during 5 min to a solution of 5-amino-2-hydroxy-pentanoic acid (17.0 g, 0.128 mol) in 0.5 M NaOH (240 mL) and dioxan (240 mL) at 5° C. The mixture was stirred for 2.5 h at room temperature. During this time 0.5 M NaOH was added to maintain pH 9-10. The dioxan was removed under reduced pressure and the aqueous phase was washed with diethyl ether. The aqueous phase was acidified to pH 2-3 with $KHSO_4$ and extracted with ethyl acetate (3×300 mL). The pooled organic phases was washed with water and brine, dried and concentrated under reduced pressure to give crude 5-tert-butoxycarbonylamino-2-hydroxy-pentanoic acid (22.0 g, 73.7%).

(b) 5-tert-Butoxycarbonylamino-2-hydroxy-pentanoic acid methyl ester

A solution of methyl iodide (11.5 mL, 0.189 mol) in DMF (50 mL) was added dropwise during 15 min. to a mixture of 5-tert-butoxycarbonylamino-2-hydroxy-pentanoic acid (22.0 g, 94.4 mmol) and $NaHCO_3$ (11.8 g, 141 mmol) in DMF (150 mL). After stirring over night, water was added and the mixture was extracted with ethyl acetate. The pooled organic phases were washed with water and brine, dried and concentrated under reduced pressure. The crude product was purified using chromatography (heptane/ethyl acetate, 1:1) to give 5-tert-butoxycarbonylamino-2-hydroxy-pentanoic acid methyl ester 9.9 g, 42.5%).

(c) 2-[(1-Benzyloxycarbonylamino-2-methyl-propyl)-methoxy-phosphinoyloxy]-5-tert-butoxycarbonylamino-pentanoic acid methyl ester A solution of PyBOP (2.1 g, 4.0 mmol) in DMF (3 mL) was added to a mixture of (1-benzyloxycarbonylamino-2-methyl-propyl)-phosphonic acid monomethyl ester (1.0 g, 3.32 mmol) and 5-tert-butoxycarbonylamino-2-hydroxy-pentanoic acid methyl ester (865 mg, 3.5 mmol) in DMF (4 mL) under argon. DIPEA (2.28 mL, 13.3 mmol) was added dropwise and the mixture was stirred over night. Ethyl acetate was added and the mixture was washed with 10% KHSO$_4$, satd. NaHCO$_3$ and brine and dried. Concentration under reduced pressure followed by chromathography (heptane/EtOAc, 1:1→1:6) gave 2-[(1-benzyloxycarbonylamino-2-methyl-propyl)-methoxy-phosphinoyloxy]-5-tert-butoxycarbonylamino-pentanoic acid methyl ester (1.21 g, 69%).

(d) 2-[(1-Benzyloxycarbonylamino-2-methyl-propyl)-hydroxy-phosphinoyloxy]-5-tert-butoxycarbonylamino-pentanoic acid 1 M LiOH (5 mL) was added to a solution of 2-[(1-benzyloxycarbonylamino-2-methyl-propyl)-methoxy-phosphinoyloxy]-5-tert-butoxycarbonylamino-pentanoic acid methyl ester (187 mg, 0.35 mmol) in acetonitrile (5 mL). The mixture was stirred at 50° C. over night and concentrated under reduced pressure. The crude product was purified using chromathography (iPrOH/conc. aq. NH$_3$/H$_2$O, 4:2:1) to yield 2-[(1-benzyloxycarbonylamino-2-methyl-propyl)-hydroxy-phosphinoyloxy]-5-tert-butoxycarbonylamino-pentanoic acid (180 mg, 100%).

(e) 5-Amino-2-[(1-benzyloxycarbonylamino-2-methyl-propyl)-hydroxy-phosphinoyloxy]-pentanoic acid TFA (3 mL) was added to a solution of 2-[(1-benzyloxycarbonylamino-2-methyl-propyl)-hydroxy-phosphinoyloxy]-5-tert-butoxycarbonylamino-pentanoic acid (150 mg, 0.3 mmol) in methylene chloride/acetonitrile (1:1, 15 mL). The solution was stirred for 120 min and concentrated under reduced pressure to give the title compound as the TFA salt (174 mg, 100%).

$^1$H NMR (500 MHz, CD$_3$OD): δ 1.02 (t, 6H), 1.66-2.0 (m, 4H), 2.23 (m, 1H), 2.93 (m, 2H), 3.91 (m, 1H), 4.85 (bs, 1H), 5.12 (m, 2H), 7.28-7.42 (m, 5H). MS (+) 403.3 (M+1).

Example 2

2-[(1-Benzyloxycarbonylamino-2-methyl-propyl)-hydroxy-phosphinoyloxy]-5-guanidino-pentanoic acid (a) 2-[(1-Benzyloxycarbonylamino-2-methyl-propyl)-hydroxy-phosphinoyloxy]-5-guanidino-pentanoic acid A solution of S-methylisothiourea hydrogen sulfate (25 mg, 90 μmol) in 1 M NaOH (0.18 mL) was added to a solution of 5-amino-2-[(1-benzyloxycarbonylamino-2-methyl-propyl)-hydroxy-phosphinoyloxy]-pentanoic acid (36 mg, 90 μmol) and 1 M NaOH (0.18 mL) in water/MeOH (1:1, 0.4 mL). The rection mixture was stirred at 50° C. for 6 h and concentrated under reduced pressure. The crude product was purified using HPLC (0-50% acetonitrile, 0.1% TFA in water) to give the title compound as the TFA salt (19 mg, 38%).

$^1$H NMR (500 MHz, CD$_3$OD): δ 1.02 (t, 6H), 1.60-1.98 (m, 4H), 2.23 (m, 1H), 3.20 (m, 2H), 3.91 (m, 1H), 4.81 (bs, 1H), 5.11 (m, 2H), 7.26-7.42 (m, 5H). MS (+) 445 (M+1).

Example 3

5-Amino-2-{[1-(2-benzyloxycarbonylamino-3-phenyl-propionylamino)-2-methyl-propyl]-hydroxy-phosphinoyloxy}-pentanoic acid (a) 2-{[1-(2-Benzyloxycarbonylamino-3-phenyl-propionylamino)-2-methyl-propyl]-hydroxy-phosphinoyloxy}-5-tert-butoxycarbonylamino-pentanoic acid methyl ester Thionyl chloride (49 μL, 0.67 mmol) was added dropwise to a solution of [1-(2-benzyloxycarbonylamino-3-phenyl-propionylamino)-2-methyl-propyl]-phosphonic acid (208 mg, 0.48 mmol) in DMF (5 mL) at −20° C. under argon. The mixture was stirred for 35 min at −5° C. A solution of 5-tert-Butoxycarbonylamino-2-hydroxy-pentanoic acid methyl ester (166 mg, 0.67 mmol) in DMF (1 mL) was added and the mixture was stirred for 90 min at room temperature. Ethyl acetate was added and the mixture was washed with 1 M HCl, dried and concentrated under reduced pressure. The crude product was purified using chromathography (CHCl$_3$/MeOH/H$_2$O, 10:1:0→10:5:1) to give 2-{[1-(2-benzyloxycarbonylamino-3-phenyl-propionylamino)-2-methyl-propyl]-hydroxy-phosphinoyloxy}-5-tert-butoxycarbonylamino-pentanoic acid methyl ester (211 mg, 66%).

(b) 2-{[1-(2-Benzyloxycarbonylamino-3-phenyl-propionylamino)-2-methyl-propyl]-hydroxy-phosphinoyloxy}-5-tert-butoxycarbonylamino-pentanoic acid 1 M LiOH (3.5 mL) was added to a solution of 2-{[1-(2-benzyloxycarbonylamino-3-phenyl-propionylamino)-2-methyl-propyl]-hydroxy-phosphinoyloxy}-5-tert-butoxycarbonylamino-pentanoic acid methyl ester (211 mg, 0.32 mmol) in acetonitrile (3.5 mL) and the mixture was stirred for 3 h. Ethyl acetate was added and the mixture was washed with 1 M HCl, dried and concentrated to give crude 2-{[1-(2-benzyloxycarbonylamino-3-phenyl-propionylamino)-2-methyl-propyl]-hydroxy-phosphinoyloxy}-5-tert-butoxycarbonylamino-pentanoic acid (208 mg, 100%).

(c) 5-Amino-2-{[1-(2-benzyloxycarbonylamino-3-phenyl-propionylamino)-2-methyl-propyl]-hydroxy-phosphinoyloxy}-pentanoic acid TFA (5 mL) was added to a solution of 2-{[1-(2-benzyloxycarbonylamino-3-phenyl-propionylamino)-2-methyl-propyl]-hydroxy-phosphinoyloxy}-5-tert-butoxycarbonylamino-pentanoic acid (208 mg, 0.32 mmol) in acetonitrile (5 mL) and the mixture was stirred for 90 min. The reaction mixture was concentrated under reduced pressure to give the crude title compound as the TFA salt (212 mg, 100%). 20 mg of the crude title compound was purified using chromathography (iPrOH/conc. aq. NH$_3$/H$_2$O, 4:2:1) to give the title compound as the TFA salt (19 mg, 94%).

$^1$H NMR (500 MHz, CD$_3$OD): δ 0.85-0.95 (m, 6H), 1.70-2.0 (m, 4H), 2.05-2.13 (m, 1H), 2.85-3.05 (m, 2H), 3.05-3.12 (m, 1H), 4.10 (bs, 1H), 4.55 (m, 1H), 4.90 (m, 1H), 5.09 (s, 2H), 7.20-7.35 (m, 10H).

Example 4

2-{[1-(2-Benzyloxycarbonylamino-3-phenyl-propionylamino)-2-methyl-propyl]-hydroxy-phosphinoyloxy}-5-guanidino-pentanoic acid (a) 5-Amino-2-hydroxy-pentanoic acid methyl ester TFA (2 mL) was added to a solution of 5-tert-butoxycarbonylamino-2-hydroxy-pentanoic acid methyl ester in methylene chloride (10 mL) and the mixture was stirred for 3 h and then concentrated under reduced pressure to give crude 5-amino-2-hydroxy-pentanoic acid methyl ester (1 g).

(b) 5-(Guanidino-ω, ω'-bis(tert-Butoxycarbonyl)-2-hydroxy-pentanoic acid methyl ester To a solution of 5-amino-2-hydroxy-pentanoic acid methyl ester (0.5 g, 2.0 mmol) in acetonitrile (5 mL) was added tert-butoxycarbonylimino-pyrazol-1-yl-methyl)-carbamic acid tert-butyl ester (0.77 g, 2.5 mmol) followed by DIPEA (0.86 mL, 5 mmol). After stirring for 60 min ethyl acetate was added. The mixture was washed with 1 M HCl, satd. NaHCO$_3$ and brine, dried and concentrated under reduced pressure. The crude product was purified using chromathography (heptane/ethyl acetate, 1:0→1:3) to give 5-(guanidino-ω, ω'-bis(tert-butoxycarbonyl)-2-hydroxy-pentanoic acid methyl ester (0.27 g, 35%).

(c) 2-{[1-(2-Benzyloxycarbonylamino-3-phenyl-propionylamino)-2-methyl-propyl]-hydroxy-phosphinoyloxy}-5-[guanidino-ω, ω'-bis(tert-Butoxycarbonyl)]-pentanoic acid methyl ester Thionyl chloride (70 μL, 0.97 mmol) was added dropwise to a solution of [1-(2-benzyloxycarbonylamino-3-phenyl-propionylamino)-2-methyl-propyl]-phosphonic acid (301 mg, 0.69 mmol) in DMF (5 mL) at −20° C. under argon. The mixture was stirred for 20 min at −5° C. A solution of 5-(guanidino-ω, ω'-bis(tert-Butoxycarbonyl)-2-hydroxy-pentanoic acid methyl ester (270 mg, 0.69 mmol) in DMF (1 mL) was added and the mixture was stirred for 180 min at room temperature. Ethyl acetate was added and the mixture was washed with 1 M HCl, dried and concentrated under reduced pressure. The crude product was purified using chromathography (toluene/ethyl acetate, 1:1→0:1) to give 2-{[1-(2-benzyloxycarbonylamino-3-phenyl-propionylamino)-2-methyl-propyl]-hydroxyphosphinoyloxy}-5-[guanidino-ω, ω'-bis(tert-butoxycarbonyl)]-pentanoic acid methyl ester (0.27 g, 48%).

(d) 2-{[1-(2-Benzyloxycarbonylamino-3-phenyl-propionylamino)-2-methyl-propyl]-hydroxy-phosphinoyloxy}-5-[guanidino-ω, ω'-bis(tert-Butoxycarbonyl)]-pentanoic acid A solution of LiOH (42 mg, 1.0 mmol) in water (1.0 mL) was added to a solution of 2-{[1-(2-benzyloxycarbonylamino-3-phenyl-propionylamino)-2-methyl-propyl]-hydroxy-phosphinoyloxy}-5-[guanidino-ω, ω'-bis(tert-butoxycarbonyl)]-pentanoic acid methyl ester (160 mg, 0.2 mmol) in acetonitrile (1.0 mL) and the mixture was stirred for 15 min. Ethyl acetate was added and the mixture was washed with 1 M HCl and brine, dried and concentrated to give crude 2-{[1-(2-benzyloxycarbonylamino-3-phenyl-propionylamino)-2-methyl-propyl]-hydroxy-phosphinoyloxy}-5-[guanidino-ω, ω'-bis(tert-butoxycarbonyl)]-pentanoic acid (160 mg, 100%).

(e) 2-{[1-(2-Benzyloxycarbonylamino-3-phenyl-propionylamino)-2-methyl-propyl]-hydroxy-phosphinoyloxy}-5-guanidino-pentanoic acid TFA (2 mL) was added to a solution of 2-{[1-(2-benzyloxycarbonylamino-3-phenyl-propionylamino)-2-methyl-propyl]-hydroxy-phosphinoyloxy}-5-[guanidino-ω, ω'-bis(tert-butoxycarbonyl)]-pentanoic acid (160 mg, 0.2 mmol) in acetonitrile (5 mL) and the mixture was stirred for 60 min and then concentrated under reduced pressure. The crude product was purified using chromathography (iPrOH/conc. aq. NH$_3$/H$_2$O, 4:2:1) to give the title compound as the TFA salt (30 mg, 21%).

$^1$H NMR (500 MHz, CD$_3$OD): δ 0.80-0.98 (m, 6H), 1.53-1.95 (m, 4H), 2.01-2.30 (m, 1H), 2.90 (m, 1H), 3.10-3.30 (m, 3H), 3.94-4.10 (m, 1H), 4.41-4.55 (m, 1H), 4.68 (m, 1H), 5.03 (m, 2H), 7.18-7.37 (m, 5H). MS (+) 592 (M+1).

Example 5

2-Hydroxycarbamoyl-4-piperidin-4-yl-butyric acid (a) Piperidin-4-yl-acetic acid

Pyridin-4-yl-acetic acid hydrochloride (20.0 g, 115 mmol) was added to water/25% ammonia (125 mL:10 mL). The mixture was degassed and flushed with nitrogen before addition of rhodium on activated alumina (0.45 g). The mixture was again degassed, then stirred in a hydrogen atmosphere at 50 bar for 16 h. Filtration of the reaction mixture through filter paper afforded the bulk of the catalyst which was recycled after washing with methanol. The filtrate was then filtered through Celite and concentrated to afford a white solid (19.7 g, 96% yield).

(b) 4-Carboxymethyl-piperidine-1-carboxylic acid tert-butyl ester

To a solution of piperidin-4-yl-acetic acid (19.7 g, 148 mmol) in THF-water (417 mL, 1:1) was added di-tert-butyl dicarbonate (32.3 g, 148 mmol) and sodium bicarbonate (12.5 g, 148 mmol), and the reaction stirred at room temperature for 16 h. THF was then removed under reduced pressure and the aqueous phase extracted with dichloromethane and the organic layer discarded. The aqueous layer was then acidified to pH 1-2 with 1 M HCl solution and extracted with ethyl acetate. The organic phase was washed with brine, dried and concentrated under reduced pressure to give 4-carboxymethyl-piperidine-1-carboxylic acid tert-butyl ester (16.7 g, 46%).

(c) 4-(2-Hydroxy-ethyl)-piperidine-1-carboxylic acid tert-butyl ester

To a solution of 4-carboxymethyl-piperidine-1-carboxylic acid tert-butyl ester (16.7 g, 69.0 mmol) in THF (100 mL) was added diborane (151 mL, 1.0 M solution in THF) over a period of 10 min at 0° C. Hydrogen gas was rapidly evolved and after gas evolution had ceased the reaction was stirred at room temperature for 1 h. The reaction mixture was again cooled to 0° C. and 1 M aqueous HCl was added dropwise to the reaction mixture with further evolution of hydrogen. Addition of HCl was continued until the evolution of hydrogen had almost ceased. The mixture was then stirred for 10 min and made basic (pH 13-14) by the addition of 1 M NaOH solution. The aqueous solution was extracted with ethyl acetate, the organic phase washed with brine, dried and concentrated under reduced pressure to yield 4-(2-hydroxyethyl)-piperidine-1-carboxylic acid tert-butyl ester (15.2 g, 97%).

(d) 4-(2-Oxo-ethyl)-piperidine-1-carboxylic acid tert-butyl ester

Periodinane (36.1 g, 85.2 mmol) was added to 4-(2-hydroxy-ethyl)-piperidine-1-carboxylic acid tert-butyl ester (15.0 g, 65.5 mmol) in CH$_2$Cl$_2$ (230 mL) and stirred for 90 min. Diethyl ether (560 ml) was added and precipitates were removed by extraction with 10% Na$_2$S$_2$O$_3$/saturated NaHCO$_3$ (1:1, 350 mL). The organic layer was washed with 0.5 M NaOH solution and brine. The organic phase was dried and concentrated under reduced pressure to yield 4-(2-Oxo-ethyl)-piperidine-1-carboxylic acid tert-butyl ester (8.50 g, 57%).

(e) 4-[2-(2,2-Dimethyl-4,6-dioxo-[1,3]dioxan-5-yl)-ethyl]-piperidine-1-carboxylic acid tert-butyl ester To a solution of meldrums acid (1.68 g, 11.66 mmol) and 4-(2-oxo-ethyl)-piperidine-1-carboxylic acid tert-butyl ester (2.21 g, 9.72 mmol) in dichloromethane (40 mL) was added acetic acid (0.055 mL, 0.972 mmol) and piperidine (0.096 mL, 0.972 mmol). The mixture was heated at reflux for 3 h, and then allowed to attain room temperature. After being diluted with tert-butyl methyl ether, the mixture was washed with NaHCO$_3$ (sat.) and brine. The organic phase was dried, filtered and concentrated. The residue was dissolved in a mixture of EtOH (40 mL) and acetic acid (20 mL). The solution was cooled to 0° C., and NaBH$_4$ (0.554 g, 14.6 mmol) was added in portions after which the solution was allowed to stir for 30 min at rt and then acidified to pH 3 with 1 M HCl. The solution was extracted several times with dichloromethane. The combined organic phases were dried, filtered, concentrated and filtered through a pad of silica gel (dichloromethane). The solvent was evaporated to give 4-[2-(2,2-Dimethyl-4,6-dioxo-[1,3]dioxan-5-yl)-ethyl]-piperidine-1-carboxylic acid tert-butyl ester as a colorless oil (2.30 g, 65%) which solidified on standing.

(f) 2-Hydroxycarbamoyl-4-piperidin-4-yl-butyric acid

A GC-autosample vial (2 mL) equipped with a septum cap and a small stirbar was charged with 4-[2-(2,2-Dimethyl-4,6-dioxo-[1,3]dioxan-5-yl)-ethyl]-piperidine-1-carboxylic acid tert-butyl ester (17.8 mg, 0.05 mmol) and flushed with nitrogen. N,O-Bis(trimethylsilyl)-hydroxylamine (0.2 mL) was added via syringe and the resulting solution was stirred at rt over night. The mixture was concentrated under vacuum and the residue dissolved in dichloromethane/MeOH (4:1) and applied onto a small plug of ion exchange resin (200 mg, isolute™, aminoresin), washed with dichloromethane/MeOH (4:1) and then eluted with dichloromethane/MeOH/AcOH (3:1:1). The eluate was concentrated, the residue dissolved in dichloromethane/TFA (1:1, 2 mL) and stirred for 1 h at room temperature. Evaporation of the solvent gave the title compound as the TFA salt (16 mg, 93%) as a colourless oil.

$^1$H NMR (600 MHz, CD$_3$OD): δ 1.21-1.40 (m, 4H), 1.53-1.62 (m, 1H), 1.80-1.99 (m, 4H), 2.90-2.98 (m, 2H), 3.06 (t, 1H), 3.32-3.39 (m, 2H). M (+) 231 (M+1).

Example 6

N-hydroxy-2-piperidin-3-ylmethyl-malonamic acid (a) 3-Hydroxymethyl-piperidine-1-carboxylic acid tert-butyl ester 3-Hydroxymethyl-piperidine (20.0 g, 0.17 mmol) in acetonitrile was treated with di-tert-butyl dicarbonate (37.9 g, 0.17 mol) and DMAP (2.13 g, 1.74 mmol). The reaction mixture was stirred at ambient temperature for 5 h and then concentrated under reduced pressure. The crude product was purified by flash chromatography (hexane/EtOAc, 70:30) to give 3-hydroxymethyl-piperidine-1-carboxylic acid tert-butyl ester (16.0 g, 44%).

(b) 3-Formyl-piperidine-1-carboxylic acid tert-butyl ester

Periodinane (18.2 g, 42.9 mmol) was added to 3-hydroxymethyl-piperidine-1-carboxylic acid tert-butyl ester (7.10 g, 33.0 mmol) in CH$_2$Cl$_2$ (230 mL) and stirred for 90 min. Diethyl ether (230 mL) was added and precipitates were removed by extraction with 10% Na$_2$S$_2$O$_3$/saturated NaHCO$_3$ (1:1, 230 mL). The organic layer was washed with 0.5 M NaOH solution and brine. The organic phase was dried and concentrated under reduced pressure to yield 3-Formyl-piperidine-1-carboxylic acid tert-butyl ester (6.50 g, 93%).

(c) N-Hydroxy-2-piperidin-3-ylmethyl-malonamic acid

The title compound was prepared from 3-formyl-piperidine-1-carboxylic acid tert-butyl ester by the method described in Example 5. Yield: (50%).

$^1$H NMR (600 MHz, CD$_3$OD): δ 1.18-1.30 (m, 1H), 1.61-1.99 (m, 6H), 2.64 (t, 1H), 2.86 (t, 1H), 3.20-3.38 (m, 3H). M (+) 217 (M+1).

Example 7

2-(6-Amino-pyridin-3-ylmethyl)-N-hydroxy-malonamic acid

The title compound was prepared from (5-Formyl-pyridin-2-yl)-carbamic acid tert-butyl ester by the method described in Example 5. Yield: (23%).

$^1$H NMR (600 MHz, CD$_3$OD): d 2.99-3.10 (m, 2H), 3.36-4.01 (m, 1H), 6.94 (d, 1H), 7.64 (s, 1H), 7.82 (d, 1H). M (+) 226 (M+1).

Example 8

2-(2-Amino-pyridin-4-ylmethyl)-N-hydroxy-malonamic acid (a) (4-Formyl-pyridin-2-yl)-carbamic acid tert-butyl ester (4-Hydroxymethyl-pyridin-2-yl)-carbamic acid tert-butyl ester (1.91 g, 8.51 mmol) was dissolved in dry DMSO (10 mL) and the reaction flask immersed in a waterbath at 15° C. Triethylamine (1.72 g, 17.0 mmol) was added followed by sulfur trioxide pyridine complex (2.41 g, 15.1 mmol). The reaction mixture was stirred for 2 h and poured onto crushed ice and the product extracted with CHCl$_3$. The organic extract was washed with water, dried concentrated under reduced pressure. The crude product was purified by flash chromatography (hexane/EtOAc, 80:20) to give (4-Formyl-pyridin-2-yl)-carbamic acid tert-butyl ester (1.57 g, 83%).

(b) 2-(2-Amino-pyridin-4-ylmethyl)-N-hydroxy-malonamic acid

The title compound was prepared from (4-Formyl-pyridin-2-yl)-carbamic acid tert-butyl ester by the method described in Example 5. Yield: (48%).

$^1$H NMR (600 MHz, CD$_3$OD): δ 3.10 (dd, 1H), 3.19 (dd, 1H), 3.47 (dd, 1H), 6.77 (d, 1H), 7.82 (s, 1H), 7.71 (d, 1H). M (+) 226 (M+1).

Example 9

2-[2-(1-tert-Butoxycarbonyl-piperidin-4-yl)-ethyl]-malonic acid

To a solution of 4-[2-(2,2-Dimethyl-4,6dioxo-[1,3]dioxan-5-yl)-ethyl]-piperidine-1-carboxylic acid tert-butyl ester (17.8 mg, 0.05 mmol) in acetic acid (1 mL) was added 6 M HCl (2 mL). The solution was stirred at room temperature over night and then concentrated to yield the title compound as the hydrochloric acid salt (15 mg, 100%).

$^1$H NMR (600 MHz, CD$_3$OD): δ 1.30-1.40 (m, 4H), 1.57-1.64 (m, 1H), 1.83-1.90 (m, 1H), 1.90-1.98 (m, 1H), 3.31-3.39 (m, 2H). M (+) 216 (M+1).

Example 10

2-[2-(1-tert-Butoxycarbonyl-piperidin-3-yl)-methyl]-malonic acid

The title compound was prepared from 3-(2,2-Dimethyl-4,6-dioxo-[1,3]dioxan-5-ylmethyl)-piperidine-1-carboxylic acid tert-butyl ester by the method described in Example 9. Yield: (100%).

$^1$H NMR (600 MHz, CD$_3$OD): δ 1.20-1.30 (m, 1H), 1.63-1.76 (m, 1H), 1.78-1.97 (m, 5H), 2.65 (t, 1H), 2.83-2.92 (m, 1H), 3.29-3.38 (m, 2H), 3.42-3.48 (m, 1H). M (+) 202 (M+1).

Example 11

2-[2-(1-tert-Butoxycarbonyl-piperidin-4-yl)-methyl]-malonic acid (a) Piperidine-1,4-dicarboxylic acid mono-tert-butyl ester Piperidine-4-carboxylic acid (24.5 g, 0.19 mmol) in THF/water (1:1, 417 mL) was treated with di-tert-butyl dicarbonate (41.49 g, 0.19 mol) and sodium bicarbonate (16.0 g, 0.19 mol). The reaction mixture was stirred at ambient temperature for 16 h. The THF was then removed under reduced pressure and the aqueous phase washed with dichloromethane. The aqueous layer was then acidified to pH 1-2 with 1 M HCl solution and extracted with ethyl acetate. The organic phase was washed with brine and dried to give piperidine-1,4-dicarboxylic acid mono-tert-butyl ester (35.9 g, 83%).

(b) 4-Hydroxymethyl-piperidine-1-carboxylic acid tert-butyl ester

To a solution of piperidine-1,4-dicarboxylic acid mono-tert-butyl ester (19.3 g, 84.0 mmol) in THF (100 mL) was added diborane (185 mL, 1.0 M solution in THF) over a period of 10 min at 0° C. Hydrogen gas was rapidly evolved and after gas evolution had ceased the reaction was stirred at room temperature for 1 h. The reaction mixture was again cooled to 0° C., and 1 M aqueous HCl was added dropwise to the reaction mixture with further evolution of hydrogen. Addition of HCl was continued until the evolution of hydrogen had almost ceased. The mixture was then stirred for 10 min and made basic (pH 13-14) by the addition of 1 M NaOH solution. The aqueous solution was extracted with ethyl acetate, the organic phase washed with brine, dried and concentrated under reduced pressure to yield 4-Hydroxymethyl-piperidine-1-carboxylic acid tert-butyl ester (18.12 g, 100%).

(c) 4-Formyl-piperidine-1-carboxylic acid tert-butyl ester

Periodinane (26.9 g, 63.5 mmol) was added to 4-Hydroxymethyl-piperidine-1-carboxylic acid tert-butyl ester (10.5 g, 48.8 mmol) in $CH_2Cl_2$ (200 ml) and stirred for 90 min. Diethyl ether (560 mL) was added and precipitates were removed by extraction with 10% $Na_2S_2O_3$/saturated $NaHCO_3$ (1:1, 300 mL). The organic layer was washed with 0.5 M NaOH solution and brine. The organic phase was dried and concentrated under reduced pressure. Purification using flash chromatography (hexane/EtOAc, 8:2) gave 4-Formyl-piperidine-1-carboxylic acid tert-butyl ester (8.5 g, 81%).

(d) 2-[2-(1-tert-Butoxycarbonyl-piperidin-4-yl)-methyl]-malonic acid

The title compound was prepared from 4-Formyl-piperidine-1-carboxylic acid tert-butyl ester by the method described in Example 5 and 9. Yield: (100%).

$^1$H NMR (600 MHz, $CD_3OD$): δ 1.38-1.48 (m, 2H), 1.61-1.75 (m, 1H), 1.82-1.90 (m, 2H), 1.92-2.02 (m, 2H), 2.90-3.01 (m, 2H), 3.35-3.42 (m, 2H), 3.42-3.48 (m, 1H). M (+) 202 (M+1).

Example 12

2-(6-tert-Butoxycarbonylamino-pyridin-3-ylmethyl)-malonic acid

The title compound was prepared from [5-(2,2-Dimethyl-4,6-dioxo-[1,3]dioxan-5-ylmethyl)-pyridin-2-yl]-carbamic acid tert-butyl ester by the method described in Example 9. Yield: (100%).

$^1$H NMR (600 MHz, $CD_3OD$): δ 3.08 (d, 2H), 3.66 (t, 1H), 6.98 (d, 1H), 7.73 (s, 1H), 7.92 (d, 1H). M (+) 211 (M+1).

Example 13

2-(2-tert-Butoxycarbonylamino-pyridin-4-ylmethyl)-malonic acid

The title compound was prepared from [4-(2,2-Dimethyl-4,6-dioxo-[1,3]dioxan-5-ylmethyl)-pyridin-2-yl]-carbamic acid tert-butyl ester by the method described in Example 9. Yield: (100%).

$^1$H NMR (600 MHz, $CD_3OD$): δ 3.10 (d, 2H), 3.79 (t, 1H), 6.84 (d, 1H), 7.92 (s, 1H), 7.77 (d, 1H). M (+) 211 (M+1).

Example 14

2-(2-Amino-pyridin-4-ylmethyl)-succinic acid (a) 2-(2-tert-Butoxycarbonylamino-pyridin-4-ylmethylene)-succinic acid 4-benzyl ester 1-tert-butyl ester Butyllithium (1.6 M in hexane, 14.8 ml, 23.7 mmol) was added dropwise to a solution of 2-(diethoxy-phosphoryl)-succinic acid 4-benzyl ester 1-tert-butyl ester (9.50 g, 23.7 mmol in THF (75 mL) at 0° C. under nitrogen. After stirring at 0° C. for 1 h, the solution was transferred to a solution of (4-Formyl-pyridin-2-yl)-carbamic acid tert-butyl ester (3.70 g, 16.6 mmol) in THF (75 mL). The resulting reaction mixture was stirred at 0° C. for 1 h before being allowed to warm to 25° C., and the mixture was stirred overnight. Water (400 mL) was added and the product extracted with $CH_2Cl_2$ (3×50 mL). The combined organic layers were dried and concentrated. Flash chromatography (hexane/EtOAc, 4:1) gave 2-(2-tert-Butoxycarbonylamino-pyridin-4-ylmethylene)-succinic acid 4-benzyl ester 1-tert-butyl ester 4.30 g (55%).

(b) 2-(2-tert-Butoxycarbonylamino-pyridin-4-ylmethyl)-succinic acid 1-tert-butyl ester 2-(2-tert-Butoxycarbonylamino-pyridin-4-ylmethylene)-succinic acid 4-benzyl ester 1-tert-butyl ester (2.81 g, 7.60 mmol) and Pd/C (10%, 400 mg) were suspended in EtOH and hydrogenated at 41 atm. and 28° C. for 3 days. The catalyst was removed from the reaction mixture by filtration. The catalyst was washed with EtOH (96%). 1 M $K_2CO_3$ (30 mL) was added to the filtrate followed by addition of water (50 mL). After 2 days the reaction mixture was evaporated to ca 80 mL, then brine (10 mL) was added and the reaction mixture extracted with ether. The aqueous phase was acidified to pH=3 and extracted with chloroform. Methanol (25 mL) was added and the reaction mixture was dried ($Na_2SO_4$+$CaSO_4$) and filtered to give 2-(2-tert-butoxycarbonylamino-pyridin-4-ylmethyl)-succinic acid 1-tert-butyl ester (1.90 g, 83%).

(c) 2-(2-Amino-pyridin-4-ylmethyl)-succinic acid

To a solution of 2-(2-tert-butoxycarbonylamino-pyridin-4-ylmethyl)-succinic acid 1-tert-butyl ester (164 mg, 0.43 mmol) in methylene chloride (1.5 mL) was added TFA (1.5 mL). The reaction mixture was stirred for 2.5 h and then concentrated under reduced pressure. The residue was lyophilized to give the title compound as the TFA salt (126 mg, 87%).

$^1$H NMR (500 MHz, $D_2O$): δ 2.58-2.80 (m, 2H), 2.88-3.07 (m, 2H), 3.13-3.26 (m, 1H), 6.79-6.84 (dd, 1H), 6.84-6.88 (s, 1H), 7.69-7.75 (d, 1H). MS (+) 225 (M+1).

Example 15 trans-2-(4-Amino-cyclohexylmethyl)-succinic acid (a) 4-[N-(tert-Butoxycarbonyl)amino]-cyclohexane carboxylic acid To a solution of cis-4-aminocyclohexane carboxylic acid (9.90 g, 69.0 mmol) in water (120 mL) and dioxane (120 mL) was added KOH (3.73 g, 56 mmol) followed by di-tert-butyl dicarbonate (15.3 g, 70.0 mmol). The reaction mixture was stirred at room temperature overnight. Water was added and the product was extracted with $CHCl_3$. The combined organic extracts were washed with water, dried and concentrated under reduced pressure to give 4-[N-(tert-butoxycarbonyl)amino]-cyclohexane carboxylic acid (14.1 g, 84%).

(b) [4-(Methoxy-methyl-carbamoyl)-cyclohexyl]-carbamic acid tert-butyl ester

A solution of 4-[N-(tert-butoxycarbonyl)amino]-cyclohexane carboxylic acid (11.95 g, 49.0 mmol), O,N-dimethylhydroxylamine (4.88 g, 50.0 mmol), DCC (9.60 g, 50 mmol) and triethylamine (5.06 g, 50.0 mmol) in DMF (150 mL) was stirred at room temperature overnight. Water (500 mL) was added and the mixture was extracted with $CHCl_3$. The organic phase was washed with water, dried and concentrated under reduced pressure. Purification by flash chromatography (hexane/EtOAc 1:1) gave [4-(methoxy-methyl-carbamoyl)-cyclohexyl]-carbamic acid tert-butyl ester (8.50 g, 61%).

(c) (4-Formyl-cyclohexyl)-carbamic acid tert-butyl ester

[4-(Methoxy-methyl-carbamoyl)-cyclohexyl]-carbamic acid tert-butyl ester (7.50 g, 26.2 mmol) in dry ether (150 ml) was reduced with an excess $LiAlH_4$. The reaction mixture was quenched by careful addition of water and extracted with $CHCl_3$. The mixture was dried and concentrated under reduced pressure to give (4-formyl-cyclohexyl)-carbamic acid tert-butyl ester (6.30 g, 93%).

(d) trans-[4-(Benzylimino-methyl)-cyclohexyl]-carbamic acid tert-butyl ester

A mixture of (4-Formyl-cyclohexyl)-carbamic acid tert-butyl ester (3.80 g, 16.7 mmol), benzylamine (1.82 g, 16.7 mmol), acetic acid (0.01 g, 16.7 mmol) and anhydrous magnesium sulfate (4.01 g, 33.3 mmol) in methylene chloride (20 mL) was stirred for 5 days. The mixture was filtered through Celite and concentrated under reduced pressure to give trans-[4-(benzylimino-methyl)-cyclohexyl]-carbamic acid tert-butyl ester (5.10 g, 97%) as a 97:3 trans:cis mixture.

(e) trans-(4-Formyl-cyclohexyl)-carbamic acid tert-butyl ester

A solution of trans-[4-(benzylimino-methyl)-cyclohexyl]-carbamic acid tert-butyl ester (2.50 g, 8.00 mmol) and oxalic acid (0.80 g) in water/THF (50 mL, 1:1) was stirred for 10 h at room temperature. The reaction mixture was concentrated under reduced pressure and methylene chloride (50 mL) was added to the residue. The organic phase was dried and concentrated under reduced pressure to give trans-(4-Formyl-cyclohexyl)-carbamic acid tert-butyl ester (1.3 g, 80%).

(f) trans 2-(4-tert-Butoxycarbonylamino-cyclohexylmethylene)-succinic acid 4-benzyl ester 1-tert-butyl ester Butyllithium (1.6 M in hexane, 5.0 ml, 8.00 mmol) was added dropwise to a solution of 2-(diethoxy-phosphoryl)-succinic acid 4-benzyl ester 1-tert-butyl ester (3.21 g, 8.00 mmol) in THF (25 mL) at 0° C. under nitrogen. After stirring at 0° C. for 1 h, the solution was transferred to a solution of trans-(4-Formyl-cyclohexyl)-carbamic acid tert-butyl ester (1.30 g, 5.72 mmol) in THF (10 mL). The resulting mixture was stirred at 0° C. for 1 h and at room temperature overnight. Water was added and the product extracted with $CH_2Cl_2$. The organic phase was dried and concentrated under reduced pressure. Flash chromatography (hexane/EtOAc, 80:20) gave trans-2-(4-tert-Butoxycarbonylamino-cyclohexylmethylene)-succinic acid 4-benzyl ester 1-tert-butyl ester (1.10 g).

(g) trans-2-(4-tert-Butoxycarbonylamino-cyclohexylmethyl)-succinic acid 1-tert-butyl ester A solution of trans-2-(4-tert-Butoxycarbonylamino-cyclohexylmethylene)-succinic acid 4-benzyl ester 1-tert-butyl ester (243 mg, 0.51 mmol) and palladium (5% on charcoal) in ethanol (15 mL) was hydrogenated at 4 bar for 3 h. The catalyst was removed from the reaction mixture by filtration. The catalyst was washed with ethanol and the solution was concentrated under reduced pressure to give crude trans-2-(4-tert-Butoxycarbonylamino-cyclohexylmethyl)-succinic acid 1-tert-butyl ester (217 mg, >100%).

(h) trans-2-(4-Amino-cyclohexylmethyl)-succinic acid

To a solution of trans-2-(4-tert-Butoxycarbonylamino-cyclohexylmethyl)-succinic acid 1-tert-butyl ester (200 mg, 0.52 mmol) in methylene chloride (1.32 g, 15.6 mmol) was added triethylsilane (150 mg, 1.30 mmol) followed by TFA (770 mg, 6.75 mmol). The reaction mixture was stirred for 2.5 h and then concentrated under reduced pressure. Purification by HPLC (0-80% acetonitrile, 0.1% TFA in water) gave the title compound as the TFA salt (60 mg, 34%).

$^1$H NMR (500 MHz, $D_2O$): δ 0.99-1.11 (m, 2H), 1.30-1.46 (m, 4H), 1.54-1.62 (m, 1H), 1.79-1.86 (m, 1H), 1.89-1.96 (m, 1H), 1.99-2.06 (m, 2H), 2.58-2.71 (m, 2H), 2.85-2.95 (m, 1H), 3.08-3.17 (m, 1H). MS (+) 230 (M+1).

Example 16

2-(6-Amino-pyridin-3-ylmethyl)-N-benzyl-N-hydroxy-succinamic acid (a) N-Benzyl-N-benzyloxy-2-(6-tert-butoxycarbonylamino-pyridin-3-ylmethyl)-succinamic acid tert-butyl ester To a solution of 2-(2-tert-butoxycarbonylamino-pyridin-4-ylmethyl)-succinic acid 1-tert-butyl ester (0.67 g, 1.76 mmol) in $CH_2Cl_2$ (25 mL) was added N-benzyl-N-benzyloxy amine (0.42 g, 1.94 mmol), DCC (0.40 g, 1.94 mmol) and DMAP (0.02 g, 0.17 mmol) and the mixture was stirred overnight. Water was added and the mixture was extracted with $CH_2Cl_2$. The organic phase was dried and filtered and the residue purified by flash chromatography (hexane/EtOAc, 4:1) to give N-Benzyl-N-benzyloxy-2-(6-tert-butoxycarbonylamino-pyridin-3-ylmethyl)-succinamic acid tert-butyl ester (0.51 g, 50%).

(b) 2-(6-Amino-pyridin-3-ylmethyl)-N-benzyl-N-benzyloxy-succinamic acid

To a solution of N-Benzyl-N-benzyloxy-2-(6-tert-butoxycarbonylamino-pyridin-3-ylmethyl)-succinamic acid tert-butyl ester (1.0 g, 1.7 mmol) in methylene chloride (10 mL) was added TFA (4 mL) at 0° C. The reaction mixture was stirred for 4 h and then concentrated under reduced pressure to give crude 2-(6-Amino-pyridin-3-ylmethyl)-N-benzyl-N-benzyloxy-succinamic acid as the TFA salt (0.9 g, 100%).

(c) 2-(6-Amino-pyridin-3-ylmethyl)-N-benzyl-N-hydroxy-succinamic acid

A solution of 2-(6-Amino-pyridin-3-ylmethyl)-N-benzyl-N-benzyloxy-succinamic acid (0.9 g, 1.7 mmol) and palladium (0.5 g, 5% on charcoal) in methanol (100 mL) was hydrogenated at 1 bar for 2 h. The reaction mixture was filtered and concentrated under reduced pressure. The residue was purified by flash chromatography (CHCl$_3$/MeOH/H$_2$O, 10:5:1) to give the title compound (123 mg, 22%).

$^1$H NMR (600 MHz, CD$_3$OD): δ 2.50-3.03 (m, 5H), 4.72 (q, 2H), 6.65 (d, 1H), 7.18-7.31 (m, 6H), 7.53 (d, 1H), 7.65 (s, 1H). MS (+) 330 (M+1).

Example 17

2-(6-amino-pyridin-3-ylmethyl)-3-[hydroxy-(3-phenyl-propyl)-phosphinoyl]-propionic acid (a) 2-(6-tert-Butoxycarbonylamino-pyridin-3-ylmethyl)-3-[hydroxy-(3-phenyl-propyl)-phosphinoyl]-propionic acid ethyl ester A solution of (3-Phenyl-propyl)-phosphinic acid (0.579 g, 3.143 mmol) and 2-(6-tert-butoxycarbonylamino-pyridin-3-ylmethyl)-acrylic acid ethyl ester (0.327 g, 1.067 mmol) in MeCN (7.5 mL) was degassed using the freeze-thaw technique. BSA (2.55 g 12.57 mmol) was added and the mixture was stirred for 3 days and concentrated under reduced pressure. The residue was dissolved in chloroform, washed with NaHCO$_3$ and brine, dried and concentrated under reduced pressure. Flash chromatography (CH$_2$Cl$_2$/MeOH, 8:2) gave 2-(6-tert-butoxycarbonylamino-pyridin-3-ylmethyl)-3-[hydroxy-(3-phenyl-propyl)-phosphinoyl]-propionic acid ethyl ester (0.240 g, 16%).

(b) 2-(6-tert-Butoxycarbonylamino-pyridin-3-ylmethyl)-3-[hydroxy-(3-phenyl-propyl)-phosphinoyl]-propionic acid To a solution of 2-(6-tert-butoxycarbonylamino-pyridin-3-ylmethyl)-3-[hydroxy-(3-phenyl-propyl)-phosphinoyl]-propionic acid ethyl ester (0.240 g, 0.489 mmol) in MeCN (3 mL) was added a solution of LiOH (0.059 g 2.45 mmol) in H$_2$O (3 mL). The mixture was then stirred at 20° C. for 1.5 hours. Ethylacetate was added and the mixture was washed with 1 M HCL and brine and filtered to give 2-(6-tert-butoxycarbonylamino-pyridin-3-ylmethyl)-3-[hydroxy-(3-phenyl-propyl)-phosphinoyl]-propionic acid (0.174 g, 77%) as white crystals.

(c) 2-(6-Amino-pyridin-3-ylmethyl)-3-[hydroxy-(3-phenyl-propyl)-phosphinoyl]-propionic acid To a mixture of 2-(6-tert-butoxycarbonylamino-pyridin-3-ylmethyl)-3-[hydroxy-(3-phenyl-propyl)-phosphinoyl]-propionic acid (0.170 g, 0.367 mmol) in ethylacetate (3 mL) at 4° C. was slowly added ethylacetate (4 mL. saturated with HCl(g)). The mixture was then stirred for 22 h. Concentration under reduced pressure gave the title compound (0.124 g, 93%) as the hydrochloride salt.

$^1$H NMR (300 MHz, CD$_3$SOCD$_3$): δ 1.52-1.72 (m, 4H), 1.88-1.96 (m, 2H), 2.47-2.49 (t, 1H), 2.57-2.62 (m, 2H), 2.77-2.82 (m, 2H), 6.94-6.97 (d, 1H), 7.15-7.29 (m, 4H), 7.75-7.80 (m, 2H), 8.05 (s, 1H). MS (+) 363 (M+1).

Example 18

2-(6-Amino-5-methyl-pyridin-3-ylmethyl)-3-[(1-benzyloxycarbonylamino-2-methyl-propyl)-hydroxy-phosphinoyl]-propionic acid (a) 2-[(1-Benzyloxycarbonylamino-2-methyl-propyl)-hydroxy-phosphinoylmethyl]-3-(6-bis(tert-butoxycarbonyl)amino-5-methyl-pyridin-3-yl)-propionic acid ethyl ester A solution of 2-(6-bis(tert-butoxycarbonyl)amino-5-methyl-pyridin-3-ylmethyl)-acrylic acid ethyl ester (0.6 g, 1.43 mmol) and (1-benzyloxycarbonylamino-2-methyl-propyl)-phosphinic acid (0.678 g, 2.5 mmol) in dry acetonitrile (10 mL) was degassed using the freeze-thaw technique. Bistrimethylsilylacetamide (5 mL, 20.3 mmol) was added under argon. The resulting mixture was stirred at room temperature for 84 h and then concentrated under reduced pressure. The remaining mixture was dissolved in chloroform and washed with saturated aqueous NaHCO$_3$. The aqueous phase was extracted with chloroform and EtOAc. The combined organic extracts were dried and concentrated under reduced pressure. The crude product was purified by flash chromatography (EtOAc/EtOH, 100:20→100:25) to yield 2-[(1-benzyloxycarbonylamino-2-methyl-propyl)-hydroxy-phosphinoylmethyl]-3-(6-bis(tert-butoxycarbonyl)amino-5-methyl-pyridin-3-yl)-propionic acid ethyl ester (650 mg, 65.9%).

(b) 2-[(1-Benzyloxycarbonylamino-2-methyl-propyl)-hydroxy-phosphinoylmethyl]3-(6-tert-butoxycarbonylamino-5-methyl-pyridin-3-yl-propionic acid 1 M LiOH (2 mL) was added dropwise to a solution of 2-[(1-benzyloxycarbonylamino-2-methyl-propyl)-hydroxy-phosphinoylmethyl]-3-(6-bis(tert-butoxycarbonyl)amino-5-methyl-pyridin-3-yl)-propionic acid ethyl ester (100 mg, 0.145 mmol) in acetonitrile (2 mL). The mixture was stirred overnight and concentrated under reduced pressure. The mixture was purified by column chromatography (isopropanol/concentrated aqueous NH$_3$/water, 4:2:1) to give impure product. The impure product was stirred with MeOH, filtered and concentrated under reduced pressure. The crude product was stirred with EtOH, filtered and concentrated under reduced pressure. The crude product was stirred with ethylacetate/ethanol, filtered and concentrated under reduced pressure to give 2-[(1-benzyloxycarbonylamino-2-methyl-propyl)-hydroxy-phosphinoylmethyl]-3-(6-tert-butoxycarbonylamino-5-methyl-pyridin-3-yl)-propionic acid (52 mg, 63.8%).

(c) 2-(6-Amino-5-methyl-pyridin-3-ylmethyl)-3-[(1-benzyloxycarbonylamino-2-methyl-propyl)-hydroxy-phosphinoyl]-propionic acid A solution of 2-[(1-benzyloxycarbonylamino-2-methyl-propyl)-hydroxy-phosphinoylmethyl]-3-(6-tert-butoxycarbonylamino-5-methyl-pyridin-3-yl)-propionic acid (52 mg, 0.09 mmol) and ethylacetate (6 mL, saturated with HCl (g)) was stirred for 20 min. The mixture was concentrated under reduced pressure, washed with acetonitrile and dissolved in ethanol and petroleumether. The solution was concentrated under reduced pressure to give the title compound (41 mg, 91.3%) as the hydrochloride salt.

$^1$H NMR (600 MHz, D$_2$O): δ 0.99-1.05 (m, 6H), 1.75-1.85 (m, 1H), 2.10-2.28 (m, 5H), 2.68-3.15 (m, 3H), 3.75-3.81 (m, 1H), 5.04-5.19 (m, 2H), 7.20-7.37 (m, 5H), 7.51-7.71 (m, 2H). MS (+) 501 (M+1)

Example 19

2-(6-Amino-pyridin-3-ylmethyl)-3-methyl-succinic acid (a) 2-Ethoxycarbonyl-3-methyl-succinic acid diethyl ester A solution of diethylmalonate (2.44 g, 15 mmol) and cesium fluoride (2.32 g, 15 mmol) in DMF (20 mL) was stirred for 1 h at room temperature under argon. A solution of 2-methanesulfonyloxy-propionic acid ethyl ester (1.0 g, 5 mmol) in DMF (5 mL) was added and the mixture was stirred at 45° C. overnight. The mixture was poured into H$_2$O and extracted with ethyl acetate. The organic layers were washed with water, dried, and concentrated under reduced pressure. The crude product was purified by vacuum distillation. The product was purified by column chromatography (petroleumether/ethyl acetate, 4:1) to give 2-(6-amino-pyridin-3-ylmethyl)-3-methyl-succinic acid (0.5 g, 37.7%).

(b) 2-(6-tert-Butoxycarbonylamino-pyridin-3-ylmethyl)-2-ethoxycarbonyl-3-methyl-succinic acid diethyl ester A solution of 2-(6-amino-pyridin-3-ylmethyl)-3-methyl-succinic acid (300 mg, 1.15 mmol) and NaH (30 mg, 1.25 mmol) in DMF (1 mL) was stirred at room temperature for 1 h under argon. A solution of (5-bromomethyl-pyridin-2-yl)-carbamic acid tert-butyl ester (330 mg, 1.15 mmol) in DMF (1 mL) was added and the reaction mixture was stirred for 24 h. The reaction was poured into $H_2O$ and extracted with ethyl acetate. The organic layer was washed with water, dried and concentrated under reduced pressure. The product was purified by column chromatography (petroleumether/ethyl acetate, 4:1) to give 2-(6-tert-butoxycarbonylamino-pyridin-3-ylmethyl)-2-ethoxycarbonyl-3-methyl-succinic acid diethyl ester (220 mg, 40.9%).

(c) 2-(6-Amino-pyridin-3-ylmethyl)-3-methyl-succinic acid

A solution of 2-(6-tert-butoxycarbonylamino-pyridin-3-ylmethyl)-2-ethoxycarbonyl-3-methyl-succinic acid diethyl ester (94 mg, 0.20 mmol) in concentrated aqueous HCl (4 mL) was stirred at reflux overnight. The mixture was concentrated under reduced pressure and freeze dried to give the title compound as the HCl salt (50 mg, 90.3%).

$^1$H NMR (400 MHz, $D_2O$): δ 1.22-1.35 (m, 3H), 2.77-3.08 (m, 4H), 6.99-7.05 (d, 1H), 7.70 (s, 1H), 7.84-7.91 (m, 1H). MS (+) 239 (M+1)

Example 20

2-(6-Amino-pyridin-3-ylmethyl)-3-phenethyl-succinic acid (a) 2-Ethoxycarbonyl-3-phenethyl-succinic acid diethyl ester A solution of diethylmalonate (240.2 mg, 1.5 mmol) and NaH (43.2 mg, 1.8 mmol) in THF (3 ml) was stirred for one hour at room temperature under argon. 2-(4-Nitro-benzenesulfonyloxy)-4-phenyl-butyric acid ethyl ester (590 mg, 1.5 mmol) and DMPU (192.2 mg, 1.5 mmol) was added and the mixture was stirred at room temperature for three days. The reaction was poured into $H_2O$ and extracted with ethyl acetate. The organic layer was washed with water and concentrated under reduced pressure. The product was purified by column chromatography (petroleumether/ethyl acetate, 4:1) to give 2-ethoxycarbonyl-3-phenethyl-succinic acid diethyl ester (274 mg, 52.1%).

(b) 2-(6-tert-Butoxycarbonylamino-pyridin-3-ylmethyl)-2-ethoxycarbonyl-3-phenethyl-succinic acid diethyl ester A solution of 2-(6-amino-pyridin-3-ylmethyl)-3-phenethyl-succinic acid (9.3 mg, 0.027 mmol) and NaH (1.39 mg, 0.032 mmol) in DMF (0.5 ml) was stirred for 15 minutes at room temperature. (5-Bromomethyl-pyridin-2-yl)-carbamic acid tert-butyl ester (8.76 mg, 0.031 mmol) was added and the mixture was stirred at room temperature over night. The reaction was poured into $H_2O$ and extracted with ethyl acetate. The organic layer was washed with water and concentrated under reduced pressure. The product was purified by column chromatography (heptane/ethyl acetate, 2:1) to give 2-(6-tert-butoxycarbonyl-amino-pyridin-3-ylmethyl)-2-ethoxycarbonyl-3-phenethyl-succinic acid diethyl ester (3.8 mg, 25.7%).

(c) 2-(6-Amino-pyridin-3-ylmethyl)-3-phenethyl-succinic acid

A solution of 2-(6-tert-butoxycarbonylamino-pyridin-3-ylmethyl)-2-ethoxycarbonyl-3-phenethyl-succinic acid diethyl ester (94 mg, 0.169 mmol) in concentrated HCl (7 ml) was stirred at reflux for 24 hours. The mixture was concentrated under reduced pressure and freeze dried to give the title compound as the HCl salt (55 mg, 99.2%).

$^1$H NMR (400 MHz, $D_2O$): δ 1.63-1.98 (m, 2H), 2.42-2.85 (m, 4H), 3.00-3.60 (m, 2H), 6.85-6.98 (m, 1H), 7.10-7.29 (m, 5H), 7.76-8.05 (m, 2H). MS (+) 329 (M+1)

Example 21

2-(6-Amino-pyridin-3-ylmethyl)-3-butyl-succinic acid (a) 2-Butyl-3-ethoxycarbonyl-succinic acid diethyl ester A solution of diethylmalonate (3.589 g, 0.022 mol) and cesium fluoride (3.406 g, 0.024 mol) in DMF (50 ml) was stirred for one hour at room temperature under argon. 2-Bromo-hexanoic acid ethyl ester (5 g, 0.022 mol) was added and the mixture was stirred at 100° C. and then at 65° C. over night. The reaction was poured into $H_2O$ and extracted with ethyl acetate. The organic layer was washed with water and concentrated under reduced pressure. The product was purified by column chromatography (heptane/ethyl acetate, 1:2) to give 2-butyl-3-ethoxycarbonyl-succinic acid diethyl ester (5.0 g, 73.8%).

(b) 2-(6-tert-Butoxycarbonylamino-pyridin-3-ylmethyl)-3-butyl-2-ethoxycarbonyl-succinic acid diethyl ester A solution of 2-butyl-3-ethoxycarbonyl-succinic acid diethyl ester (1 g, 3 mmol) and NaH (119 mg, 5 mmol) in DMF (20 ml) was stirred for 60 minutes at 0° C. under argon. (5-Bromomethyl-pyridin-2-yl)-carbamic acid tert-butyl ester (1.425 g, 5 mmol) was added and the mixture was stirred at room temperature for one week. Ethanol (1 ml) was added and the reaction was poured into $H_2O$ and extracted with ethyl acetate. The organic layer was washed with water and concentrated under reduced pressure. The product was purified by column chromatography (heptane/ethyl acetate, 4:1 to 1:1) to give 2-(6-tert-butoxycarbony-lamino-pyridin-3-ylmethyl)-3-butyl-2-ethoxycarbonyl-succinic acid diethyl ester (1.2 g, 71.3%).

(c) 2-(6-Amino-pyridin-3-ylmethyl)-3-butyl-succinic acid

A solution of 2-(6-tert-butoxycarbonylamino-pyridin-3-ylmethyl)-3-butyl-2-ethoxycarbonyl-succinic acid diethyl ester (50 mg, 0.098 mmol) in concentrated HCl (4 ml) was stirred at reflux for 24 hours. The mixture was concentrated under reduced pressure and freeze dried to give the title compound as the HCl salt (28 mg, 89.9%).

$^1$H NMR (400 MHz, $D_2O$): δ 0.83-0.91 (m, 3H), 1.18-1.40 (m, 4H), 1.50-1.82 (m, 2H), 2.67-2.75 (m, 12H), 2.78-2.85 (m, 2H), 2.89-3.03 (m, 1H), 6.97-7.09 (m, 1H), 7.63-7.67 (m, 1H), 7.80-7.85 (m, 1H). MS (+) 281 (M+1)

ABBREVIATION

Ac=acetate
aq=aqueous
AIBN=α,α'-azoisobutyronitrile
Bn=benzyl
BSA=N,O-bis(trimethylsilyl)acetamide
Bu=butyl
Bz=benzoyl
DCC=dicyclohexylcarbodiimide DIAD=diisopropyl azodicarboxylate
DIPEA=diisopropylethylamine
DMAP=N,N-dimethyl amino pyridine
DME=1,2-dimethoxyethane
DMF=dimethylformamide
DMSO=dimethylsulfoxide
EDC=1-(3-dimethylaminopropyl)-3-ethylcarbodiimide
Et=ethyl
EtOAc=ethyl acetate
EtOH=ethanol
h=hour
HMDS=hexamethyldisilazane
HOAc=acetic acid
HOBt=1-hydroxybenzotriazol
HPLC=high performance liquid chromatography
KHMDS=potassium bis(trimethylsilyl)amide
LDA=lithium diisopropylamide
Me=methyl
MeOH=methanol
min=minutes
PMB=4-methoxybenzyl
Ph=phenyl
Pr=propyl
PyBOP=(benzotriazol-1-yloxy)tripyrrolidinophosphonium hexafluorophosphate
TEA=triethylamine
TFA=trifluoroacetic acid
THF=tetrahydrofuran
TMSCN=trimethylsilyl cyanide
Tos=toluene-4-sulfonyl That which is claimed:

1. A compound of general formula I

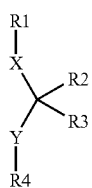

(I)

or a pharmaceutically acceptable salt or solvate thereof, wherein:

$R_1$ is selected from the group consisting of:
  $C_1$-$C_6$ alkyl, substituted with one or more basic groups selected from amino, amidino and guanidino;
  six-membered aromatic heterocyclyl containing a single heteroatom, which heteroatom is nitrogen, and substituted with one or more basic groups selected from amino, amidino and guanidino; and
  six-membered aliphatic heterocyclyl containing a single heteroatom, which heteroatom is nitrogen;

$R_2$ is selected from the group consisting of H, methyl, halogen, and hydroxy;

$R_3$ is selected from the group consisting of $COOR_5$, $SO(OR_5)$, $SO_3R_5$, $B(OR_5)_2$, $P=O(R_5)(OR_5)$, tetrazole, and a carboxylic acid isostere;

$R_4$ represents a

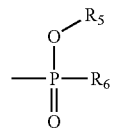

-group;

$R_5$ is H, $C_1$-$C_6$ alkyl, or aryl;
$R_6$ is $C_1$-$C_6$ alkyl, aryl, cycloalkyl, or an optionally N-substituted $H_2N$—CH(Z)—CONH—CH(Z)— or $H_2N$—CH(Z)— group;
X is $C(Z)_2$;
Y is selected from the group consisting of O and S; and
Z is independently selected from the group consisting of H, $C_1$-$C_6$ alkyl, aryl, and cycloalkyl.

2. The compound according to claim 1, or a pharmaceutically acceptable salt or solvate thereof, wherein:
$R_1$ is selected from the group consisting of:
  six-membered aromatic heterocyclyl containing a single heteroatom, which heteroatom is nitrogen, and substituted with one or more basic groups selected from amino, amidino and guanidino; and
  six-membered aliphatic heterocyclyl containing a single heteroatom, which heteroatom is nitrogen;
$R_3$ is $COOR_5$;
Y is O; and
Z is independently H or $C_1$-$C_6$ alkyl.

3. The compound according to claim 1 or a pharmaceutically acceptable salt or solvate thereof, wherein:
$R_6$ is optionally substituted by one or more selected from the group consisting of acyl, acylamino, $C_1$-$C_6$ alkyl, alkylcarbamoyl, alkylthio, alkoxy, aroyl, aroylamino, aryloxy, arylthio, amidino, amino, aryl, carbamoyl, carboxy, cyano, cycloalkyl, formyl, guanidine, halogen, hydroxy, oxo, nitro, thio, $Z_2N$—CO—O—, ZO—CO—NZ— and $Z_2N$—CO—NZ—;
in which said $C_1$-$C_6$ alkyl, cycloalkyl, and aryl are each optionally substituted by one or more selected from the group consisting of acyl, acylamino, $C_1$-$C_6$ alkyl, alkylcarbamoyl, alkylthio, alkoxy, aroyl, aroylamino, aryloxy, arylthio, amidino, amino, aryl, carbamoyl, carboxy, cyano, cycloalkyl, formyl, guanidino, halogen, hydroxy, oxo, nitro, thio, $Z_2N$—CO—O—, ZO—CO—NZ— and $Z_2N$—CO—NZ—; and
each Z, which is defined in claim 1, is independently and optionally substituted by one or more selected from the group consisting of acyl, acylamino, $C_1$-$C_6$ alkyl, alkylcarbamoyl, alkylthio, alkoxy, aroyl, aroylamino, aryloxy, arylthio, amidino, amino, aryl, carbamoyl, carboxy, cyano, cycloalkyl, formyl, guanidino, halogen, hydroxy, oxo, nitro, thio, $Z_2N$—CO—O—, ZO—CO—NZ— and $Z_2N$—CO—NZ—.

4. The compound according to claim 3 or a pharmaceutically acceptable salt or solvate thereof, wherein:
$R_6$ is optionally substituted by one or more selected from the group consisting of $C_1$-$C_6$ alkyl, aryl and ZO—CO—NZ—,
in which said $C_1$-$C_6$ alkyl and aryl are each optionally substituted by one or more selected from the group consisting of aryl, oxo and ZO—CO—NZ—, and
each Z, which is defined in claim 1, is independently and optionally substituted by aryl.

5. A process for the preparation of a compound according to any one of claims 1, 2, 3 and 4, wherein $R_1$, $R_2$, $R_4$, $R_5$, $R_6$, X and Z are as defined in claim 1, $R_3$ is $COOR_5$, and Y is O, comprising the step of:

reacting a compound of Formula XII,

wherein X, $R_1$ and $R_2$ are as defined in claim 1, with a compound of Formula XIII,

wherein $R_6$ is as defined in claim 1, in the presence of a coupling reagent under standard conditions.

6. A pharmaceutical formulation comprising a therapeutically effective amount of a compound according to any one of claims 1, 2, 3 and 4 as active ingredient in combination with a pharmaceutically acceptable adjuvant, diluent, or carrier.

7. A method for inhibiting carboxypeptidase U, comprising administering an effective amount of a compound according to any one of claims 1, 2, 3 and 4.

8. A pharmaceutical formulation comprising:
(i) a compound of Formula I as defined in any one of claims 1, 2, 3 and 4, or a pharmaceutically acceptable salt or solvate thereof; and
(ii) one or more antithrombotic agents with a different mechanism of action from that of component (i), in admixture with a pharmaceutically acceptable adjuvant, diluent, or carrier.

9. A method both for inhibiting carboxypeptidase U and for achieving an antithrombotic effect via a different mechanism, which method comprises administering a therapeutically effective total amount of:

(i) a compound as defined in any one of claims 1, 2, 3 and 4, or a pharmaceutically acceptable salt or solvate thereof, in admixture with a pharmaceutically acceptable adjuvant, diluent, or carrier; and
(ii) one or more antithrombotic agents with a different mechanism of action from that of component (i), in admixture with a pharmaceutically acceptable adjuvant, diluent, or carrier.

10. A method both for inhibiting carboxypeptidase U and for achieving an antithrombotic effect via a different mechanism, which method comprises administering the formulation according to claim 8.

11. The process according to claim 5, wherein the coupling reagent is selected from the group consisting of:
(i) dicyclohexylcarbodiimide (DCC)/N,N-dimethyl amino pyridine (DMAP);
(ii) (benzotriazol-1-yloxy)tripyrrolidinophosphonium hexafluorophosphate (PyBop)/diisopropylethylamine (DIPEA); and
(iii) $SOCl_2$.

12. The formulation according to claim 8, wherein the antithrombotic agent with a different mechanism of action is selected from the group consisting of an antiplatelet agent, thromboxane receptor inhibitor, synthetase inhibitor, fibrinogen receptor antagonist, prostacyclin mimetic, phosphodiesterase inhibitor, and an ADP-receptor ($P_2T$) antagonist.

13. The method according to claim 9, wherein the antithrombotic agent with a different mechanism of action is selected from the group consisting of an antiplatelet agent, thromboxane receptor inhibitor, synthetase inhibitor, fibrinogen receptor antagonist, prostacyclin mimetic, phosphodiesterase inhibitor, and an ADP-receptor ($P_2T$) antagonist.

14. A method for treatment of thrombosis and hypercoagulability, comprising administering to a patient in need of such treatment an effective amount of a compound according to any one of claims 1, 2, 3 and 4.

* * * * *

UNITED STATES PATENT AND TRADEMARK OFFICE
CERTIFICATE OF CORRECTION

PATENT NO. : 7,354,895 B1
APPLICATION NO. : 09/600660
DATED : April 8, 2008
INVENTOR(S) : Linschoten et al.

It is certified that error appears in the above-identified patent and that said Letters Patent is hereby corrected as shown below:

Claim 1, col. 31, line 51; claim 2, col. 32, line 21; claim 3, col. 32, line 33; claim 4, col. 32, line 59; claim 8, col. 33, line 32; and claim 9, col. 34, line 2: in each instance, delete "or solvate".

Claim 3, col. 32, line 38: "guanidine" should read --guanidino--.

Signed and Sealed this

Twenty-fifth Day of November, 2008

JON W. DUDAS
*Director of the United States Patent and Trademark Office*